US006395939B1

(12) United States Patent
Marcoux et al.

(10) Patent No.: US 6,395,939 B1
(45) Date of Patent: May 28, 2002

(54) DIARYL ETHER CONDENSATION REACTIONS

(75) Inventors: Jean-Francois Marcoux, Westfield, NJ (US); Sven Doye, Hannover (DE); Stephen Buchwald, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/166,760

(22) Filed: Oct. 5, 1998

Related U.S. Application Data

(60) Provisional application No. 60/061,114, filed on Oct. 6, 1997.

(51) Int. Cl.[7] .......................... C07C 41/01; C07C 41/09
(52) U.S. Cl. .......................... 568/635; 568/17; 568/58; 568/315; 568/585; 568/627; 568/636; 568/639; 560/64; 562/473; 562/899; 556/64; 564/305
(58) Field of Search .................. 568/635, 627, 568/585, 639, 636, 315, 17, 58; 560/64; 562/473, 899; 564/305; 556/64

(56) References Cited

U.S. PATENT DOCUMENTS

| 4,222,962 A | | 9/1980 | Pellegrini, Jr. ............... 260/571 |
| 4,288,386 A | | 9/1981 | Soula et al. ................ 260/465 |
| 4,316,994 A | * | 2/1982 | Fuchs et al. ................ 568/639 |
| 4,404,400 A | | 9/1983 | Heise et al. ................ 564/406 |
| 4,422,955 A | | 12/1983 | Bryant ....................... 502/169 |
| 4,495,353 A | | 1/1985 | Bryant ....................... 546/178 |
| 4,564,712 A | | 1/1986 | Kuckertz et al. ............ 568/635 |
| 4,642,349 A | * | 2/1987 | Renga ........................ 546/302 |
| 4,694,110 A | * | 9/1987 | Takenaka et al. ........... 568/638 |
| 4,709,081 A | | 11/1987 | Heja et al. .................. 560/100 |
| 4,766,253 A | * | 8/1988 | Rauber ....................... 568/639 |
| 4,771,062 A | | 9/1988 | Raddatz et al. ............. 514/370 |
| 4,902,826 A | | 2/1990 | Bauer et al. ................ 562/432 |
| 5,576,460 A | | 11/1996 | Buchwald et al. .......... 564/386 |
| 5,648,539 A | | 7/1997 | Goodbrand ................. 564/309 |
| 5,654,482 A | | 8/1997 | Goodbrand ................. 564/405 |

FOREIGN PATENT DOCUMENTS

| DE | 4427120 A1 | 2/1996 |
| EP | 0 024 019 A1 | 7/1980 |
| EP | 0 040 140 A1 | 11/1981 |
| EP | 0 051 235 B1 | 1/1985 |
| EP | 0 202 838 A2 | 12/1986 |
| EP | 0 431 487 A1 | 11/1990 |
| GB | 2025403 A | 3/1978 |
| JP | 04257553 A | 9/1992 |

OTHER PUBLICATIONS

Afzeli, A, et al., "Improved Ullmann Synthesis of Diaryl Ethers," *Synthetic Communications*, 13(4), pp. 335–339 (1983).

Boger, D.L., et al., "Total Synthesis of Deoxybouvardin and RA–VII: Macrocyclization via an Intramolecular Ullmann Reaction," *J. Am. Chem. Soc.* 1991, vol. 113, No. 4, pp. 1427–1429.

Boger, D.L., et al., "Vancomycin and Restocetin Models: Synthesis via the Ullmann Macrocyclization Reaction," *J. Org. Chem.* 1993, vol. 58, No. 6, pp. 1425–1433.

Boger, D. L., et al., "Intramolecular Ullmann Condensation Reaction: An Effective Approach to Macrocyclic Diaryl Ethers," *J. Org. Chem.* 1991, vol. 56, No. 5, 1763–1767.

Cava, M. P., et al., "A Practical Route to Bisbenzylisoquinolines by an Improved Ullman Diphenyl Ether Synthesis," *J. Org. Chem.*, vol. 40, No. 11, 1975, pp. 1553–1556.

Marcoux, J., et al., "A General Copper–Catalyzed Synthesis of Diaryl Ethers," *J. Am. Chem. Soc.*, 1997, vol. 119, No. 43, pp. 10539–10540.

Oi, R., et al., "Ullmann Ether Synthesis in DMI. Preparation of m–Phenoxybenzyl Alchol," *The Chemical Society of Japan*, Chemistry Letters, 1988, pp. 899–900.

Pellon, R.F., et al., "Use of Pyridine as Cocatalyst for the Synthesis of 2–Carboxy Substituted Diphenylethers by Ullmann–Goldberg Condensation," *Synthetic Communications*, 25(7), pp. 1077–1083 (1995).

Rama Rao, A.V., "Ortho–Nitro–Promoted Ullmann Ether Synthesis: Application in the Syntheses of K–13 and the Isodityrosine unit of Vancomycin," *Tetrahedron Letters*, vol. 33, No. 33, pp. 4799–4802 (1992).

Rewcastle, G.W., et al., "The Synthesis of 9–Oxo–9, 10–Dihydroacridine–4–Carboxylic Acids Via the Jourdan–Ullmann Reaction of Anthranilic Acids and Methyl 2–Iodobenzoates," *Synthetic Communications*, 17(3), pp. 309–317 (1987).

Schmittling, E.A., et al., "Synthesis of Diaryl Ethers, Diaryl Thioethers, and Diarylamines Mediated by Potassium Fluoride–Alumina and 18–Crown–6," *J. Org. Chem.*, vol. 58, No. 12, pp. 3229–3230 (1993).

Smith, K., et al., "A Superior Synthesis of Diaryl Ethers by the Use of Ultrasound in the Ullmann Reaction," *J. Chem. Soc. Perkin Trans. 1*, pp. 407–408 (1992).

Williams, A.L., et al., "Solvent–Assisted Ullmann Ether Synthesis. Reactions of Dihydric Phenols," *Solvent–Assisted Ullmann Ether Synthesis*, Aug. 1967, pp. 2501–2505.

\* cited by examiner

*Primary Examiner*—Rosalynd Keys
(74) *Attorney, Agent, or Firm*—Dana M. Gordon; Foley, Hoag & Eliot LLP

(57) ABSTRACT

One aspect of the present invention relates to novel reaction conditions that allow the efficient synthesis of diaryl ethers from arenes bearing a leaving group and arenols under relatively mild conditions. Another aspect of the present invention relates to the dramatic effects of acidic activators on Ullmann-type couplings involving electron-poor and/or relatively insoluble substrates.

64 Claims, No Drawings

DIARYL ETHER CONDENSATION REACTIONS

RELATED APPLICATIONS

This application claims the benefit of the filing date of U.S. Provisional Application 60/061,114, filed Oct. 6, 1997.

GOVERNMENT SUPPORT

This invention was supported in part with funding provided by the National Science Foundation; the government has certain rights in the invention.

BACKGROUND OF THE INVENTION

The formation of diaryl ethers from arenols and aryl groups bearing a leaving group generally requires activated substrates. For aryloxide nucleophiles, the reaction is promoted by copper salts. For instance, Ullman (*Ber.* 37:853) observed in 1904 that the presence of metallic copper greatly facilitates the substitution of a halogen atom on an aromatic ring with a phenolic oxygen. This method for the synthesis of diaryl ethers, referred to in the contemporary art as the "Ullmann reaction" or "Ullmann condensation", has become widely used in both academic and industrial chemistry. For a review, see Moroz et al. (1974) *Russ. Chem. Rev.* 43:679.

The Ullmann reaction is typically carried out by heating the reactants at elevated temperatures, e.g., 150–300° C., in the presence of a copper salt, which in some cases is present in only a catalytic amount; Ullmann reactions are usually conducted in a solvent, however, in certain cases a solvent is not utilized (the optimal temperature for Ullmann condensations conducted without solvent is typically in range of 180–220° C.). To minimize oxidation of the phenolic reactant, the reactions are often performed under an inert atmosphere. See, for example, Weingarten et al. (1964) *J. Org. Chem.* 29:3624; and Moroz et al. supra.

The Ullmann reaction is widely used in industry, in particular, for the synthesis of various substituted diaryl ethers that are useful as pharmaceuticals, herbicides or insecticides, or as intermediates in the synthesis thereof. A wide variety of diaryl ethers have found use in, for instance, the synthesis of complex natural products. The reaction is also widely used in the general chemical industry. To illustrate, the Ullmann reaction serves as part of a method for the synthesis of phenyl ether (used to prepare heat exchangers and in the perfume industry), substituted phenyl ethers (monomers for thermostable polymers), and polyphenyl ethers, which have found important applications in, for example, oils for creation of ultrahigh vacuums, high-temperature greases, hydraulic liquids, etc.

The conditions used for the copper-mediated coupling of aryl halides and phenols according to the Ullmann reaction are usually harsh, requiring high temperatures and high-boiling, polar solvents (pyridine, collidine, DMF). The classical use of the reaction also has the usual requirement for stoichiometric (or greater) quantities of the copper reagent. The yields of the reaction are substrate dependent and are usually low for transformations involving highly functionalized substrates. For example, during the course of the total synthesis of such antibiotics as vancomycin, attempted Ullmann condensations for the coupling of advanced intermediates were unsuccessful (see, e.g., Williams (1984) *Acc Chem. Res.* 17:364). Indeed, in the synthesis of pharmaceutical agents, many of the desirable substituents on the substrate aryl moieties may not be sufficiently stable, even when protected, for use in the Ullmann reaction of the prior art. For instance, esters and anhydrides are not stable under the classical Ullmann reaction conditions.

Likewise, the conditions of the classical Ullmann reaction may be too harsh for use in a combinatorial approach to the synthesis of libraries of diaryl ethers and the like, particularly where labile groups are employed, for example, as linker groups or encoding tags (see: Ohlmeyer et al. (1993) *PNAS* 90:10922; and Brenner et al. (1992) *PNAS* 89:5381–5383).

Another problem with the classical Ullmann reaction is that many of the solvents that are characteristically relied upon are extremely hazardous. Disposal of reaction by-products, e.g., spent solvent, may accordingly pose significant obstacles, in terms of environmental safety and/or ultimate product cost, to reliance on the classical Ullmann reaction.

Recent efforts to develop Ullmann-type procedures which are applicable to more complex synthetic intermediates have met with only limited success (Evans et al. (1989) *J. Am. Chem. Soc.* 111:1063; and Boger et al. (1991) *J. Org. Chem.* 56:4204) or require the presence of an activating group on the substrate bearing the leaving group (for selected examples of activating groups, see Nicolaou et al. (1997) *J. Am. Chem. Soc.* 119:3421 and Rozanel'skaya et al. (1961) *Zhur. Obschc. Khim.* 31:758).

SUMMARY OF THE INVENTION

One aspect of the present invention relates to novel reaction conditions that allow the efficient synthesis of diaryl ethers from arenes bearing a leaving group and arenols under relatively mild conditions. Another aspect of the present invention relates to the discovery of the dramatic effects of aryl carboxylic acid additives on copper-catalyzed Ullmann-type couplings.

One aspect of the present invention provides a cross-coupling reaction, represented in the general formula:

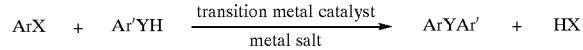

wherein

Ar and Ar' independently represent optionally substituted aryl or heteroaryl groups;

YH represents a substituent of Ar' that includes a nucleophilic group, or a group that can be rendered nucleophilic;

X represents a leaving group which can be substituted by the nucleophilic group of Y in a transition metal-catalyzed reaction;

the transition metal catalyst is a complex which catalyzes formation of ArYAr' from ArX and Ar'YH;

the metal salt has an anionic portion that is sufficiently basic to neutralize the HX produced in the reaction and/or deprotonate Ar'YH and thereby render it a better nucleophile, and the metal salt comprises a soft cation selected from the alkali metal or alkaline earth series, e.g., Rb, Cs, Fr, Sr, Ba or Ra.

In another embodiment of the present invention, the subject method is represented by the transformation above and the attendant definitions, is included in the reaction mixture.

In another embodiment of the present invention, the subject method is represented by the transformation above and the attendant definitions, wherein a stoichiometric amount of a carboxylic acid, e.g., an aryl carboxylic acid, is included in the reaction mixture.

In yet another embodiment of the present invention, the subject method is represented by the transformation above and the attendant definitions, wherein a catalytic amount, e.g., 5 mol %, of a Lewis basic additive, e.g., an ester, and a stoichiometric amount of a carboxylic acid, e.g., an aryl carboxylic acid, are included in the reaction mixture.

In another embodiment of the present invention the transformation depicted above, in any of the aforementioned embodiments, occurs in an aprotic, non-polar solvent, e.g., toluene, at about 110 C.

DETAILED DESCRIPTION OF THE INVENTION

The ability to provide an Ullmann synthesis method that can be carried out under mild conditions and/or with non-polar, aprotic solvents has broad application, especially in the agricultural, polymer, and pharmaceutical industries. The present invention provides such an Ullmann synthesis method.

One aspect of the present invention provides a mild and general procedure for the formation of diaryl ethers and the like. The subject procedure, set out in more detail below and in the Examples, is characterized by one or more of the following features:

(i) the reaction uses a sub-stoichimetric amount of a metal catalyst, such as a copper catalyst;

(ii) the reaction uses an alkali salt, the cationic portion being a soft cation of the alkali metal or alkaline earth series and (preferably) having electrons in the $4^{th}$ or higher quantum level, and the anionic portion being basic enough to deprotonate a phenolic group or the like (e.g., the nucleophilic group of Ar'YH below), wherein the alkali salt eliminates the need to form a phenoxide anion or the like prior to reaction;

(iii) the reaction can be run with good yield in a non-polar, aprotic solvent; and (iv) the reaction can be run with good yield at reaction temperatures below 130 C.

Based on the present experimental observations, the subject method may be generally represented by the following reaction scheme:

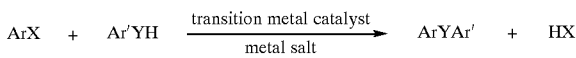

wherein

Ar and Ar' independently represent optionally substituted aryl or heteroaryl groups;

YH represents a substituent of Ar' that includes a nucleophilic group, or a group that can be rendered nucleophilic;

X represents a leaving group which can be substituted by the nucleophilic group of Y in a transition metal-catalyzed reaction;

the transition metal catalyst is a complex which catalyzes formation of ArYAr' from ArX and Ar'YH;

the metal salt has an anionic portion that is sufficiently basic to neutralize the HX produced in the reaction and/or deprotonate Ar'YH and thereby render it a better nucleophile, and the metal salt comprises a soft cation selected from the alkali metal or alkaline earth series, e.g., Rb, Cs, Fr, Sr, Ba or Ra.

In another embodiment of the present invention, the subject method is represented by the transformation above and the attendant definitions, is included in the reaction mixture.

In another embodiment of the present invention, the subject method is represented by the transformation above and the attendant definitions, wherein a stoichiometric amount of a carboxylic acid, e.g., an aryl carboxylic acid, is included in the reaction mixture.

In yet another embodiment of the present invention, the subject method is represented by the transformation above and the attendant definitions, wherein a catalytic amount, e.g., 5 mol %, of a Lewis basic additive, e.g., an ester, and a stoichiometric amount of a carboxylic acid, e.g., an aryl carboxylic acid, are included in the reaction mixture.

In another embodiment of the present invention the transformation depicted above, in any of the aforementioned embodiments, occurs in an aprotic, non-polar solvent, e.g., toluene, at about 110 C.

In certain embodiments, the present invention is represented by the generalized method depicted in scheme 1:

Scheme 1

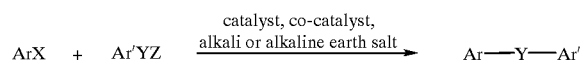

wherein

Ar and Ar' independently represent optionally substituted monocyclic or polycyclic aromatic or heteroaromatic moieties;

X represents Cl, Br, I, —O₃S(alkyl), or —O₃S(aryl);

Y represents O, S, Se, NR, PR, or AsR;

Z represents H, a group that is lost under the reaction conditions to generate a negative charge on Y, or a group that is replaced by H under the reaction conditions;

R represents H, alkyl, aryl, aralkyl, heteroalkyl, heteroaryl, trialkylsilyl, acyl, or sulfonyl;

catalyst represents a transition metal complex;

co-catalyst represents a uncharged molecule comprising a Lewis basic pair of electrons; and alkali or alkaline earth salt represents a salt selected from the group consisting of alkali and alkaline earth bicarbonates, carbonates, carboxylates, phosphates, alkoxides, silicates, amides, and sulfides.

In certain embodiments, the subject method is represented by scheme 1 and the associated definitions, wherein X represents Br or I.

In certain embodiments, the subject method is represented by scheme 1 and the associated definitions, wherein Y represents O, S, Se, or NR.

In certain embodiments, the subject method is represented by scheme 1 and the associated definitions, wherein Y represents O or S.

In certain embodiments, the subject method is represented by scheme 1 and the associated definitions, wherein Y represents O.

In certain embodiments, the subject method is represented by scheme 1 and the associated definitions, wherein Z represents H.

In certain embodiments, the subject method is represented by scheme 1 and the associated definitions, wherein Ar and Ar' independently represent optionally substituted monocyclic aryl or heteroaryl moieties.

In certain embodiments, the subject method is represented by scheme 1 and the associated definitions, wherein Ar and Ar' independently represent optionally substituted phenyl.

In certain embodiments, the subject method is represented by scheme 1 and the associated definitions, wherein the reaction occurs in a non-polar, aprotic solvent.

In certain embodiments, the subject method is represented by scheme 1 and the associated definitions, wherein the reaction occurs in an aromatic hydrocarbon solvent.

In certain embodiments, the subject method is represented by scheme 1 and the associated definitions, wherein the reaction occurs in toluene.

In certain embodiments, the subject method is represented by scheme 1 and the associated definitions, wherein the reaction occurs at a temperature in the range of about 75–150 C.

In certain embodiments, the subject method is represented by scheme 1 and the associated definitions, wherein the reaction occurs at a temperature in the range of about 90–135 C.

In certain embodiments, the subject method is represented by scheme 1 and the associated definitions, wherein the reaction occurs at a temperature in the range of about 100–120 C.

In certain embodiments, the subject method is represented by scheme 1 and the associated definitions, wherein the alkali or alkaline earth salt comprises cesium.

In certain embodiments, the subject method is represented by scheme 1 and the associated definitions, wherein the alkali or alkaline earth salt is cesium carbonate.

In certain embodiments, the subject method is represented by scheme 1 and the associated definitions, wherein the co-catalyst is an ester.

In certain embodiments, the subject method is represented by scheme 1 and the associated definitions, wherein the co-catalyst is an acetate.

In certain embodiments, the subject method is represented by scheme 1 and the associated definitions, wherein the co-catalyst is ethyl acetate.

In certain embodiments, the subject method is represented by scheme 1 and the associated definitions, wherein the catalyst comprises copper.

In certain embodiments, the subject method is represented by scheme 1 and the associated definitions, wherein the catalyst is a copper salt.

In certain embodiments, the subject method is represented by scheme 1 and the associated definitions, wherein the catalyst is selected from the group consisting of copper carboxylates, copper carbonates, copper sulfates, copper sulfonates, copper halides, copper trifluoroborates, and copper phosphates.

In certain embodiments, the subject method is represented by scheme 1 and the associated definitions, wherein the catalyst is copper triflate.

In certain embodiments, the subject method is represented by scheme 1 and the associated definitions, wherein the catalyst and co-catalyst are independently present in the range of about 0.01 to 20 mol % relative to Ar'YZ.

In certain embodiments, the subject method is represented by scheme 1 and the associated definitions, wherein the catalyst and co-catalyst are independently present in the range of about 0.1 to 10 mol % relative to Ar'YZ.

In certain embodiments, the subject method is represented by scheme 1 and the associated definitions, wherein the catalyst and co-catalyst are independently present in the range of about 1 to 5 mol % relative to Ar'YZ.

In certain embodiments, the subject method is represented by scheme 1 and the associated definitions, wherein X represents Br or I; Y represents O, S, Se, or NR; Ar and Ar' independently represent optionally substituted monocyclic aryl or heteroaryl moieties; the reaction occurs in a non-polar, aprotic solvent; the reaction occurs at a temperature in the range of about 75–150 C; the alkali or alkaline earth salt comprises cesium; the co-catalyst is an ester; the catalyst comprises copper; and the catalyst and co-catalyst are independently present in the range of about 0.01 to 20 mol % relative to Ar'YZ.

In certain embodiments, the subject method is represented by scheme 1 and the associated definitions, wherein X represents Br or I; Y represents O or S; the reaction occurs in an aromatic hydrocarbon solvent; the alkali or alkaline earth salt is cesium carbonate; the reaction occurs at a temperature in the range of about 90–135 C; the co-catalyst is an acetate; the catalyst is selected from the group consisting of copper carboxylates, copper carbonates, copper sulfates, copper sulfonates, copper halides, copper trifluoroborates, and copper phosphates; and the catalyst and co-catalyst are independently present in the range of about 0.1 to 10 mol % relative to Ar'YZ.

In certain embodiments, the subject method is represented by scheme 1 and the associated definitions, wherein X represents Br or I; Y represents O; Z represents H; the reaction occurs in toluene; the alkali or alkaline earth salt is cesium carbonate; the catalyst is copper triflate; the co-catalyst is ethyl acetate; the reaction occurs at a temperature in the range of about 100–120 C; and the catalyst and co-catalyst are independently present in the range of about 1 to 5 mol % relative to Ar'YZ.

In certain embodiments, the subject method is represented by scheme 1 and the associated definitions, or any of the embodiments described above, wherein the reaction is intramolecular.

In certain embodiments, the present invention is represented by the generalized method depicted in scheme 2:

Scheme 2

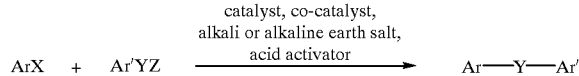

wherein
Ar and Ar' independently represent optionally substituted monocyclic or polycyclic aromatic or heteroaromatic moieties;

X represents Cl, Br, I, —O$_3$S(alkyl), or —O$_3$S(aryl);

Y represents O, S, Se, NR, PR, or AsR;

Z represents H, a group that is lost under the reaction conditions to generate a negative charge on Y, or a group that is replaced by H under the reaction conditions;

R represents H, alkyl, aryl, aralkyl, heteroalkyl, heteroaryl, trialkylsilyl, acyl, or sulfonyl;

catalyst represents a transition metal complex;

co-catalyst represents a uncharged molecule comprising a Lewis basic pair of electrons;

acid activator is selected from the group consisting of carboxylic acids, amides, hydroxamic acids, phosphoric acids, phosphonic acids, phosphinic acids, sulfonic acids, sulfinic acids, sulfenic acids, alkylboronic acids, arylboronic acids, silicic acids, alcohols, and thiols; and alkali or alkaline earth salt represents a salt selected from the group consisting of alkali and alkaline earth bicarbonates, carbonates, carboxylates, phosphates, alkoxides, silicates, amides, and sulfides.

In certain embodiments, the subject method is represented by scheme 2 and the associated definitions, wherein X represents Br or I.

In certain embodiments, the subject method is represented by scheme 2 and the associated definitions, wherein Y represents O, S, Se, or NR.

In certain embodiments, the subject method is represented by scheme 2 and the associated definitions, wherein Y represents O or S.

In certain embodiments, the subject method is represented by scheme 2 and the associated definitions, wherein Y represents O.

In certain embodiments, the subject method is represented by scheme 2 and the associated definitions, wherein Z represents H.

In certain embodiments, the subject method is represented by scheme 2 and the associated definitions, wherein Ar and Ar' independently represent optionally substituted monocyclic aryl or heteroaryl moieties.

In certain embodiments, the subject method is represented by scheme 2 and the associated definitions, wherein Ar and Ar' independently represent optionally substituted phenyl.

In certain embodiments, the subject method is represented by scheme 2 and the associated definitions, wherein the reaction occurs in a non-polar, aprotic solvent.

In certain embodiments, the subject method is represented by scheme 2 and the associated definitions, wherein the reaction occurs in an aromatic hydrocarbon solvent.

In certain embodiments, the subject method is represented by scheme 2 and the associated definitions, wherein the reaction occurs in toluene.

In certain embodiments, the subject method is represented by scheme 2 and the associated definitions, wherein the reaction occurs at a temperature in the range of about 75–150 C.

In certain embodiments, the subject method is represented by scheme 2 and the associated definitions, wherein the reaction occurs at a temperature in the range of about 90–135 C.

In certain embodiments, the subject method is represented by scheme 2 and the associated definitions, wherein the reaction occurs at a temperature in the range of about 100–120 C.

In certain embodiments, the subject method is represented by scheme 2 and the associated definitions, wherein the alkali or alkaline earth salt comprises cesium.

In certain embodiments, the subject method is represented by scheme 2 and the associated definitions, wherein the alkali or alkaline earth salt is cesium carbonate.

In certain embodiments, the subject method is represented by scheme 2 and the associated definitions, wherein the co-catalyst is an ester.

In certain embodiments, the subject method is represented by scheme 2 and the associated definitions, wherein the co-catalyst is an acetate.

In certain embodiments, the subject method is represented by scheme 2 and the associated definitions, wherein the co-catalyst is ethyl acetate.

In certain embodiments, the subject method is represented by scheme 2 and the associated definitions, wherein the acid activator is selected from the group consisting of alkyl and aryl carboxylic acids, alkyl and aryl phosphonic acids, alkyl and aryl sulfonic acids, and alkyl and aryl boronic acids.

In certain embodiments, the subject method is represented by scheme 2 and the associated definitions, wherein the acid activator is selected from the group consisting of alkyl and aryl carboxylic acids.

In certain embodiments, the subject method is represented by scheme 2 and the associated definitions, wherein the acid activator is selected from the group consisting of aryl carboxylic acids.

In certain embodiments, the subject method is represented by scheme 2 and the associated definitions, wherein the acid activator is 1-naphthoic acid.

In certain embodiments, the subject method is represented by scheme 2 and the associated definitions, wherein the catalyst comprises copper.

In certain embodiments, the subject method is represented by scheme 2 and the associated definitions, wherein the catalyst is a copper salt.

In certain embodiments, the subject method is represented by scheme 2 and the associated definitions, wherein the catalyst is selected from the group consisting of copper carboxylates, copper carbonates, copper sulfates, copper sulfonates, copper halides, copper trifluoroborates, and copper phosphates.

In certain embodiments, the subject method is represented by scheme 2 and the associated definitions, wherein the catalyst is copper triflate.

In certain embodiments, the subject method is represented by scheme 2 and the associated definitions, wherein the catalyst and co-catalyst are independently present in the range of about 0.01 to 20 mol % relative to Ar'YZ.

In certain embodiments, the subject method is represented by scheme 2 and the associated definitions, wherein the catalyst and co-catalyst are independently present in the range of about 0.1 to 10 mol % relative to Ar'YZ.

In certain embodiments, the subject method is represented by scheme 2 and the associated definitions, wherein the catalyst and co-catalyst are independently present in the range of about 1 to 5 mol % relative to Ar'YZ.

In certain embodiments, the subject method is represented by scheme 2 and the associated definitions, wherein X represents Br or I; Y represents O, S, Se, or NR; Ar and Ar' independently represent optionally substituted monocyclic aryl or heteroaryl moieties; the reaction occurs in a non-polar, aprotic solvent; the reaction occurs at a temperature in the range of about 75–150 C; the alkali or alkaline earth salt comprises cesium; the acid activator is selected from the group consisting of alkyl and aryl carboxylic acids, alkyl and aryl phosphonic acids, alkyl and aryl sulfonic acids, and alkyl and aryl boronic acids; the co-catalyst is an ester; the catalyst comprises copper; and the catalyst and co-catalyst are independently present in the range of about 0.01 to 20 mol % relative to Ar'YZ.

In certain embodiments, the subject method is represented by scheme 2 and the associated definitions, wherein X represents Br or I; Y represents O or S; the reaction occurs in an aromatic hydrocarbon solvent; the alkali or alkaline earth salt is cesium carbonate; the reaction occurs at a temperature in the range of about 90–135 C; the acid activator is selected from the group consisting of alkyl and aryl carboxylic acids; the co-catalyst is an acetate; the catalyst is selected from the group consisting of copper carboxylates, copper carbonates, copper sulfates, copper sulfonates, copper halides, copper trifluoroborates, and copper phosphates; and the catalyst and co-catalyst are independently present in the range of about 0.1 to 10 mol % relative to Ar'YZ.

In certain embodiments, the subject method is represented by scheme 2 and the associated definitions, wherein X represents Br or I; Y represents O; Z represents H; the reaction occurs in toluene; the alkali or alkaline earth salt is cesium carbonate; the catalyst is copper triflate; the acid activator is 1-naphthoic acid; the co-catalyst is ethyl acetate; the reaction occurs at a temperature in the range of about 100–120 C; and the catalyst and co-catalyst are independently present in the range of about 1 to 5 mol % relative to Ar'YZ.

In certain embodiments, the subject method is represented by scheme 2 and the associated definitions, or any of the embodiments described above, wherein the reaction is intramolecular.

As described in the Examples, during a study directed to finding new methods for the preparation of diaryl ethers, it was discovered that the reaction of a phenol with an aryl halide in DMF, using a catalytic amount of copper salt and cesium carbonate at 110° C., gave the desired diaryl ether product in high yield. These reaction conditions, e.g., using cesium carbonate or its equivalent, proved to be unexpectedly efficient for this reaction with an unactivated aryl halide substrate.

The reaction using the alkali salt cesium carbonate was also carried out in less polar solvents such as THF, ethyl acetate, xylene and toluene in order to avoid the problems associated with the use of toxic, high-boiling or water soluble solvents such as DMF and pyridine. As described in the Examples, the modified Ullmann reaction was found to be effective for coupling a wide range of substituted aryl groups, activated and unactivated, and using a wide range of solvents not previously utilized with any efficiency in the Ullmann reaction conditions known in the art.

Another aspect of the invention relates to the discovery that the use of a reaction additive, namely a carboxylic acid or the like (an "acid activator"), can improve the yield of an Ullmann reaction for less soluble and/or less nucleophilic embodiments of Ar'YH, particularly in non-polar solvents. As described in the Examples, stoichiometric amounts of a carboxylic acid added to the reaction mixture can dramatically increase the conversion and yield for the coupling of less reactive phenols. In this regard, the activator is an acid selected to help solubilize key intermediates in the condensation reaction. In general, the activator will include a strongly acidic group, e.g., with a pKa less than 5, which can produce a conjugate base that, under the reaction conditions, is a strong enough Lewis base to donate an electron pair to the metal catalyst to form a coordinate bond with a cationic form of the metal. Moreover, the activator renders its complex with copper-phenoxide more soluble in the reaction solvent than the copper catalyst by itself. By use of such reaction additives, the resulting new procedure allows, for the first time, an efficient Ullmann reaction in non-polar, aprotic solvents and with less reactive and/or soluble phenols.

While not wishing to be bound by any particular theory, the nature of the cation of the alkali salt may play an important role during the formation or the solubilization of such an intermediate. Cesium phenoxides and carboxylates are known to be relatively soluble in organic solvents. See, for example, Hennings et al. (1997) *J. Org. Chem.* 62:2; Kwizinga et al. (1979) *J. Chem. Soc., Chem. Commun*, 286; and Zaugg, H. E., (1976) *J. Org. Chem.* 41:3419. In the subject method, the use of cesium carbonate (and the like) may enhance the solubility of the phenoxides, and of the possible intermediate 1, compared to the use of its potassium and sodium counterparts.

Moreover, the results presented in the Examples suggest that the role of an acid additive, e.g., 1-naphthoic acid, is not simply an acid-base effect only, but rather that it plays an integral role in the reaction. For example, addition of cesium naphthoate rendered reactive a previously unreactive mixture containing cesium phenoxide, 1-bromo-4-tert-butylbenzene, and 2.5 mol % $(CuOTf)_2.PhH$. In addition, the use of this additive allowed the reaction to proceed using potassium carbonate as a base.

Definitions

For convenience, before further description of the present invention, certain terms employed in the specification, examples, and appended claims are collected here.

The term "substrate aryl group" refers to an aryl group containing an electrophilic atom which is susceptible to the subject cross-coupling reaction, e.g., the electrophilic atom bears a leaving group.

The terms "reactive aryl group" and "nucleophilic aryl group" refer to an aryl group substituted with a nucleophilic moiety which can attack the electrophilic atom of the substrate aryl group and displace the leaving group in the subject cross-coupling reaction.

The substrate aryl group and nucleophilic aryl group can be single ring molecules, or can be substituents of larger molecules, or substituents of the same molecule (for intramolecular condensations).

The term "nucleophile" is recognized in the art, and as used herein means a chemical moiety having a reactive pair of electrons. Examples of nucleophiles include uncharged compounds such as alcohols, thiols, selenols, and amines, and charged moieties such as alkoxides, thiolates, carbanions, and a variety of other anions.

The term "electrophile" is art-recognized and refers to chemical moieties which can accept a pair of electrons from a nucleophile as defined above.

The terms "electrophilic atom", "electrophilic center" and "reactive center" as used herein refer to the atom of the substrate aryl moiety which is attacked by, and forms a new bond to, the nucleophile. In most (but not all) cases, this will also be the aryl ring atom from which the leaving group departs.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma ($\sigma$) constant. This well known constant is described in many references, for instance, J. March, *Advanced Organic Chemistry*, McGraw Hill Book Company, New York, (1977 edition) pp. 251–259. The Hammett constant values are generally negative for electron donating groups ($\sigma[P]=-0.66$ for $NH_2$) and positive for electron withdrawing groups ($\sigma[P]=0.78$ for a nitro group), $\sigma[P]$ indicating para substitution. Exemplary electron-withdrawing groups include nitro, ketone, aldehyde, sulfonyl, trifluoromethyl, —CN, chloride, and the like. Exemplary electron-donating groups include amino, methoxy, and the like.

The term "reaction product" means a compound which results from the reaction of a nucleophilic moiety of an aryl group and an electrophilic center of a substrate aryl group. In general, the term "reaction product" will be used herein to refer to a stable, isolable diaryl ether product or the like, and not to unstable intermediates or transition states.

The term "complex" as used herein and in the claims means a coordination compound formed by the union of one or more electron-rich and electron-poor molecules or atoms capable of independent existence with one or more electronically poor molecules or atoms, each of which is also capable of independent existence.

The term "catalytic amount" is recognized in the art and means a substoichiometric amount of reagent relative to a reactant. As used herein, a catalytic amount means from 0.0001 to 90 mole percent reagent relative to a reactant, more preferably from 0.001 to 50 mole percent, still more preferably from 0.01 to 10 mole percent, and even more preferably from 0.1 to 5 mole percent reagent to reactant.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 3–10 carbon atoms in their ring structure, and more preferably have 5, 6 or 7 carbons in the ring structure.

Moreover, the term "alkyl" (or "lower alkyl") as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an ester, a formyl, or a ketone), a thiocarbonyl (such as a thioester, a thioacetate, or a thioformate), an alkoxyl, a phosphoryl, a phosphonate; a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described above, for example, halogen, azide, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The abbreviations Me, Et, Ph, Tf, Nf, Ts, Ms, and dba represent methyl, ethyl, phenyl, trifluoromethanesulfonyl, nonafluorobutanesulfonyl, p-toluenesulfonyl, methanesulfonyl, and dibenzylideneacetone, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle", as used herein, refers to an aromatic or non-aromatic ring in which each atom of the ring is carbon.

The term "heteroatom" as used herein means an atom of any element other than carbon or hydrogen. Preferred heteroatoms are nitrogen, oxygen, sulfur and phosphorous.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "amine" and "amino" are art recognized and refer to both unsubstituted and substituted amines, e.g., a moiety that can be represented by the general formula:

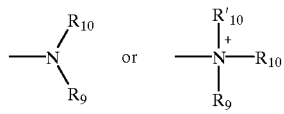

wherein $R_9$, $R_{10}$ and $R'_{10}$ each independently represent a hydrogen, an alkyl, an alkenyl, —$(CH_2)_m$—$R_8$, or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In even more preferred embodiments, $R_9$ and $R_{10}$ (and optionally $R'_{10}$) each independently represent a hydrogen, an alkyl, an alkenyl, or —$(CH_2)_m$—$R_8$. Thus, the term "alkylamine" as used herein means an amine group, as defined above, having a substituted or unsubstituted alkyl attached thereto, i.e., at least one of $R_9$ and $R_{10}$ is an alkyl group.

The term "acylamino" is art-recognized and refers to a moiety that can be represented by the general formula:

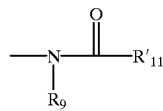

wherein $R_9$ is as defined above, and $R'_{11}$ represents a hydrogen, an alkyl, an alkenyl or —$(CH_2)_m$—$R_8$, where m and $R_8$ are as defined above.

The term "amido" is art recognized as an amino-substituted carbonyl and includes a moiety that can be represented by the general formula:

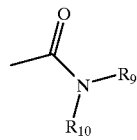

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S— alkyl, —S-alkenyl, —S-alkynyl, and —S—$(CH_2)_m$—$R_8$, wherein m and $R_8$ are defined above. Representative alkylthio groups include methylthio, ethyl thio, and the like.

The term "carbonyl" is art recognized and includes such moieties as can be represented by the general formula:

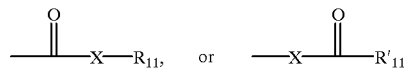

wherein X is a bond or represents an oxygen or a sulfur, and $R_{11}$ represents a hydrogen, an alkyl, an alkenyl, —$(CH_2)$ m—R8 or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "sulfonate" is art recognized and includes a moiety that can be represented by the general formula:

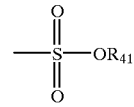

in which $R_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutane-sulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The term "sulfate" is art recognized and includes a moiety that can be represented by the general formula:

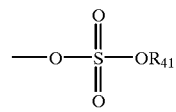

in which $R_{41}$ is as defined above.

The term "sulfonamido" is art recognized and includes a moiety that can be represented by the general formula:

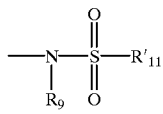

in which $R_9$ and $R'_{11}$ are as defined above.

The term "sulfamoyl" is art-recognized and includes a moiety that can be represented by the general formula:

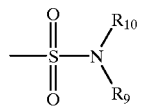

in which $R_9$ and $R_{10}$ are as defined above.

The terms "sulfoxido" or "sulfinyl", as used herein, refers to a moiety that can be represented by the general formula:

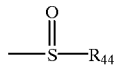

in which $R_{44}$ is selected from the group consisting of hydrogen, alkyl, alkenyl, alkynyl, cycloalkyl, heterocyclyl, aralkyl, or aryl.

A "phosphoryl" can in general be represented by the formula:

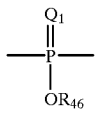

wherein $Q_1$ represented S or O, and $R_{46}$ represents hydrogen, a lower alkyl or an aryl. When used to substitute, e.g., an alkyl, the phosphoryl group of the phosphorylalkyl can be represented by the general formula:

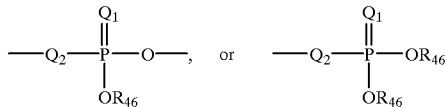

wherein $Q_1$ represented S or O, and each $R_{46}$ independently represents hydrogen, a lower alkyl or an aryl, $Q_2$ represents O, S or N. When $Q_1$ is an S, the phosphoryl moiety is a "phosphorothioate".

A "phosphoramidite" can be represented in the general formula:

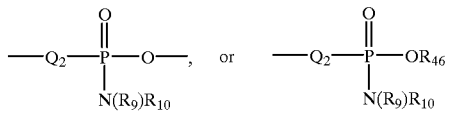

wherein $R_9$ and $R_{10}$ are as defined above, and $Q_2$ represents O, S or N.

A "phosphonamidite" can be represented in the general formula:

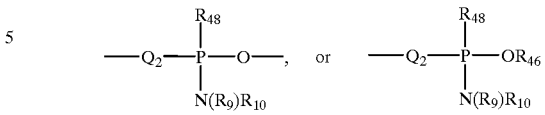

wherein $R_9$ and $R_{10}$ are as defined above, $Q_2$ represents O, S or N, and $R_{48}$ represents a lower alkyl or an aryl, $Q_2$ represents O, S or N.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_8$, m and $R_8$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The phrase "protecting group" as used herein means temporary modifications of a potentially reactive functional group which protect it from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991).

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

A "polar solvent" means a solvent which has a dielectric constant ($\epsilon$) of 2.9 or greater, such as DMF, THF, ethylene glycol dimethyl ether (DME), DMSO, acetone, acetonitrile, methanol, ethanol, isopropanol, n-propanol, t-butanol or 2-methoxyethyl ether. Preferred solvents are DMF, DME, NMP, and acetonitrile.

A "polar, aprotic solvent" means a polar solvent as defined above which has no available hydrogens to exchange with the compounds of this invention during reaction, for example DMF, acetonitrile, diglyme, DMSO, or THF.

An "aprotic solvent" means a non-nucleophilic solvent having a boiling point range above ambient temperature, preferably from about 25° C. to about 190° C., more preferably from about 80° C. to about 160° C., most preferably from about 80° C. to 150° C., at atmospheric pressure. Examples of such solvents are acetonitrile, toluene, DMF, diglyme, THF or DMSO.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

Exemplary Catalyzed Reactions

As described above, one invention of the Applicants' features a general metal-catalyzed cross-coupling reaction which comprises combining an aryl group (a "reactive aryl") having a nucleophilic moiety, an aryl group (a "substrate aryl") having an electrophilic center susceptible to attack by the nucleophilic moiety of the reactive aryl, at least a catalytic amount of a transition metal catalyst of particular characteristics (as described below), and an alkali salt derived from certain alkali metal or alkaline earth metals (the so-called "soft ions"). The combination is maintained under conditions appropriate for the metal catalyst to catalyze the nucleophilic addition of the reactive aryl to the electrophilic atom of the substrate aryl.

Another related invention of the Applicants' features a modified Ullmann reaction, similar to that described above, wherein the reaction includes the use of an acid activator, which as described herein, is an acid selected to help solubilize key intermediates in the condensation reaction. The use of such additives extends the applicability of the Ullman reaction to less soluble phenols and phenols containing electron-withdrawing groups. As described in the Examples, this modification can be combined with the modified Ullmann reaction above, e.g., with reaction profiles which include the use of a soft ion form of an alkali metal or alkaline earth metal salt, but should also be understood as useful with a wide range of other bases.

Each of the improvements to the Ullmann reaction, whether used together or separately, can be applied to cross-coupling reactions involving aryl halides and phenols. They may also be adapted to a wide range of other substituted aryls. Examples of the subject modified Ullmann reactions which may be carried out according to the present invention follow.

In an exemplary embodiment, the subject method can be used to synthesize diaryl ethers in an intermolecular reaction involving two substituted phenyl groups. For instance, the modified Ullmann reaction can be used to generate diaryl ether intermediates in the synthesis of antimitotic combretastatin analogs (see, for example, Boger et al. (1991) *J Org Chem* 56:4201). Compounds of this class have been shown to have antitumor activity. As illustrated below, 3-(3-hydroxy-4-alkoxyphenyl)-1-methoxy-1-propanol and 4-iodobenzaldehyde are reacted under appropriate conditions for the subject method.

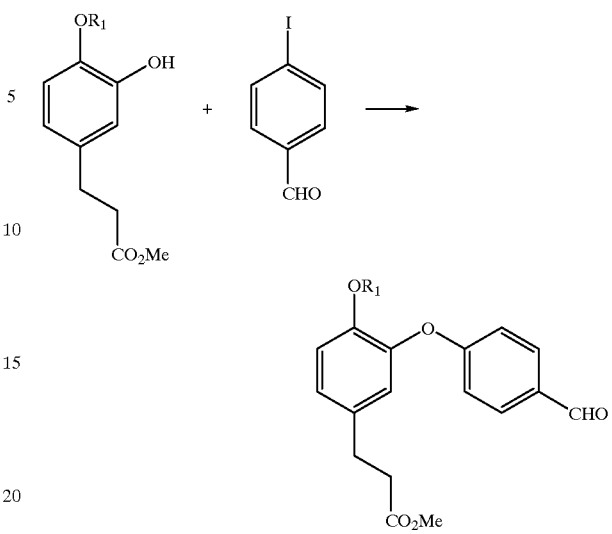

In another embodiment, the subject method can be used to synthesize diaryl ethers in which one or both of the aryl groups are polycyclic aromatics or heteroaromatic rings. As illustrated below, substituted forms of 3-bromo-2-phenylbenzo[b]thiophene and phenol can be reacted under the conditions of the subject Ullmann reactions to yield 3-phenoxy-2-phenylbenzo[b]thiophene derivatives. Such benzothiophene derivatives can be used in the treatment of post-menopausal syndrome, uterine fibroid disease, endometriosis and the like. See, for example, U.S. Pat. No. 5,510,498.

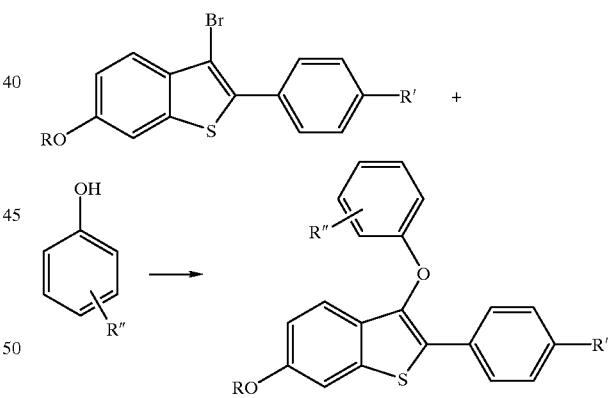

In addition to intermolecular reactions, those skilled in the art will readily appreciate that the subject modified Ullmann reaction can be used in macrocyclization reactions, e.g., in an intramolecular reaction, in which the substrate and reactive aryl groups are part of the same molecule. Returning to the combrestatin synthesis, another means for generating combrestatin analogs is based on the implementation of an intramolecular Ullmann reaction for forming the cyclic 15-membered biaryl ether. As shown below, a (Z)-3-(4-iodophenyl)-2-propenyl 3-(3-hydroxyphenyl)propanoate can be reacted according to the criteria of the subject reaction to yield combrestatin D-2 analogs.

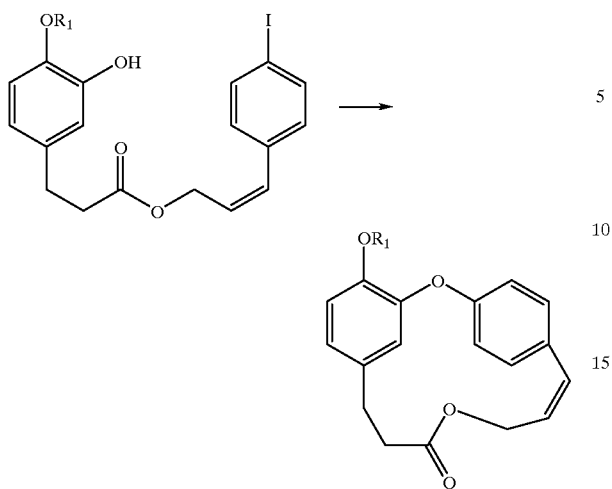

As set out above, the subject Ullmann reaction can be carried out using reactive aryl groups having other nucleophilic groups in place of a reactive hydroxyl. In certain embodiments, the reactive aryl is an amine-substituted aryl. Aminopyridines are important in various fields of chemistry. They have been used as acyl transfer reagents in organic chemistry, and ligands in organic and organometallic chemistry. Additionally, aminopyridine derivatives have been used as fluorescent dyes and are biologically important as central nervous system stimulants. In an exemplary embodiment of the subject method, 3-bromoquinoline and N-methylaniline are reacted under the conditions of the subject method to form an N-methyl-N-phenyl-3-quinolinamine (reaction scheme 6):

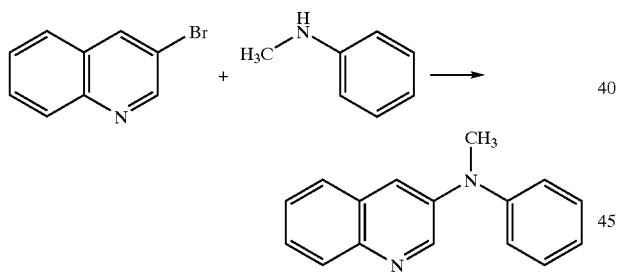

Another example of a reaction amenable to the conditions of the subject reaction is the synthesis of 1-cyano-3H-dibenz[f,ij]isoquinoline-2,7-diones. As shown below, the 1-cyano-6-bromyl-3H-dibenz[f,ij] isoquinoline-2,7-dione can be reacted with an aniline by the modified Ullmann reaction to form a diaryl amine, in this case a dye useful in toners for polyesters.

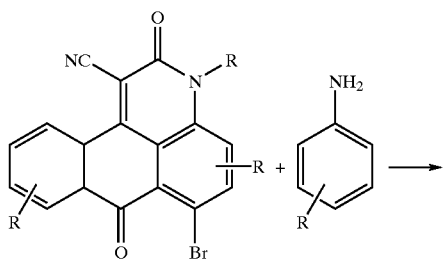

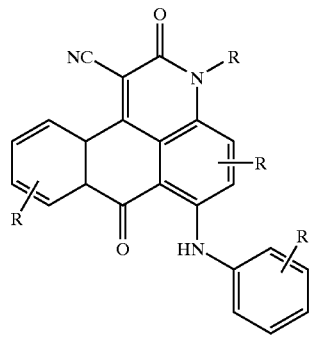

In the exemplary transformation below, the subject modified Ullmann reaction is used in the synthesis of diaryl selenoethers and diaryl thioethers. For instance, the subject method can be used to generate the 6-pyridyl substituted pyrimidines of U.S. Pat. No. 5,278,167. Such compounds are useful in the treatment of retroviral infections. In the illustrative embodiment, 6-bromo-5-ethyl-1-(phenoxymethyl)-uracil and 3-pyridineselenol can be reacted according to the conditions of the modified Ullmann reaction to yield a 5-ethyl-1-(phenoxymethyl)-6-(3-pyridylselanyl)-uracil.

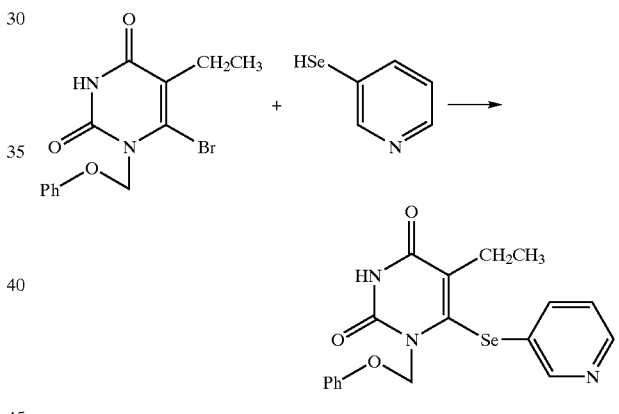

Likewise, 6-bromo-5-ethyl-1-(phenoxymethyl)-uracil and 3-pyridinethiol can be reacted according to the present method in order to yield a 5-ethyl-1-(phenoxymethyl)-6-(3-pyridylsulfanyl)-uracil.

The modified Ullmann reaction of the present invention can also be used in the synthesis of polyether compounds. As illustrated below, a halogenated 3-oxapentane compound can be reacted with a dimethyldiphenylamine under the modified Ullmann reaction conditions of the present invention to produce a diphenylamine-capped polyether polymer. Such polymers can be used as polyconductive layers in electrophotographic photoconductors. See U.S. Pat. No. 5,158,850.

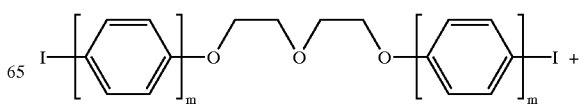

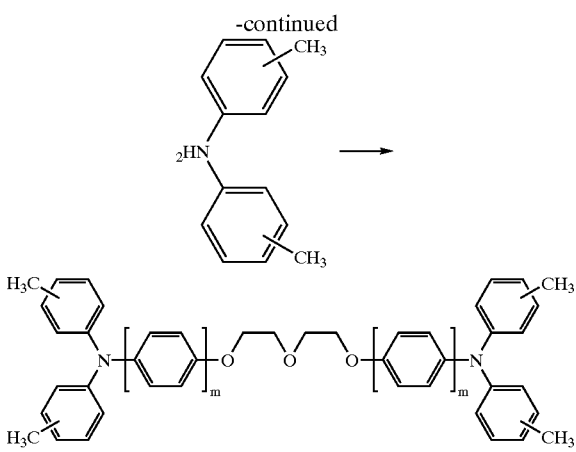

As is clear from the above discussion, the products which may be produced by the modified Ullmann reaction of this invention can undergo further reaction(s) to afford desired derivatives thereof. Such permissible derivatization reactions can be carried out in accordance with conventional procedures known in the art. For example, potential derivatization reactions include esterification, oxidation of alcohols to aldehydes and acids, N-alkylation of amides, nitrile reduction, acylation of ketones by esters, acylation of amines and the like. To further illustrate, exemplary classes of pharmaceuticals which can be synthesized by a scheme including the subject reaction are cardiovascular drugs, nonsteroidal antiinflammatory drugs, central nervous system agents, and antihistaminics.

Exemplary Aryl Reactants

As can be seen from inspection of the illustrative reaction schemes above and in the appended examples, the subject methods are generally applicable for cross-coupling of a wide range of substituted aryl groups. Examples of aryl groups which can be used in the subject reactions, e.g., as either a substrate aryl group or a reactive aryl group, include but are not limited to, substituted forms of benzene, pyrrole, furan, thiophene, imidazole, oxazole, thiazole, isothiazole, triazole, oxidiazole, pyrazole, pyridine, pyrazine, pyridazine, pyrimidine, triazine, benzofuran, isobenzofuran, indole, pyrano[3,4-b]pyrrole, indoxazine, phthalazine, anthranil, naphthalene, coumarin, isocoumarin (and other benzopyrones), quinoline, isoquinoline, cinnoline, quinazoline, naphthyridine, pyrido[3,4-b]pyridine, pyrido[3,2-b]pyridine, pyrido[4,3-b]pyridine, anthracene, benz[a]anthracene, acridine, azukene, heptalene, indacene, phenanthrene, chrysene, and the like.

In the case of the substrate aryl group (ArX), the aryl group is substituted with a leaving group which can be displaced by the nucleophilic group of the reactive aryl. In general, the leaving group is an electron-withdrawing group such as a halide, a cyano, a nitro, $+N(R)_3$, diazonium moieties, or sulfonates (such as p-toluenesulfonates (tosylates), p-bromobenzenesulfonates (brosylates), p-nitrobenzenesulfonates (nosylates), methanesulfonates (mesylates), ammonioalkane sulfonate esters (betylates), alkyl fluorosulfonates, trifluoromethanesulfonates (triflates), nonafluorobutanesulfonates (nonaflates), 2,2,2-trifluoroethanesulfonates (tresylates), and the like). In preferred embodiments, the leaving group is a halide selected from iodine and bromine. Chlorine and fluorine can also be used as leaving groups, though other electronegative substitution on the aryl group may be required to activate those halogens as leaving groups in the subject metal cross-coupling reactions.

With respect to the reactive aryl group (Ar'YH), the aryl group is substituted with a nucleophilic group, or a group that can be activated as a nucleophile, that can displace the leaving group of the substrate aryl in the subject reaction. Exemplary nucleophilic groups which can be used to substitute the reactive aryl include alcohols, thiols, selenyls, and amines. As an example of a group which can be activated as nucleophile, it is noted that in certain embodiments wherein a carboxylate is the nucleophile it will preferably masked as an ester or amide which can be activated under conditions consistent with its use in the subject modified Ullmann reaction.

In addition to the above activating substituents, both the substrate and reactive aryl groups may also be substituted with any number of a variety of groups. In this regard, the subject reaction can be represented in by the following general scheme.

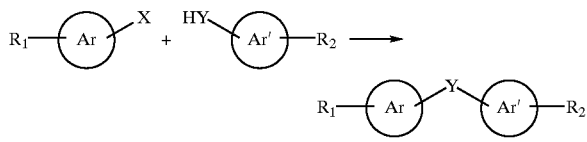

wherein, as described above, Ar and Ar' are aryl groups (of the same or different molecules), X is a leaving group, YH is nucleophilic group, and $R_1$ and $R_2$ represent one or more substitutions to the aryl groups Ar and Ar', respectively. Each incidence of substitution independently can be, as valence and stability permit, a halogen, a lower alkyl, a lower alkenyl, a lower alkynyl, a carbonyl (e.g., an ester, a carboxylate, or a formate), a thiocarbonyl (e.g., a thiolester, a thiolcarboxylate, or a thiolformate), a ketyl, an aldehyde, an amino, an acylamino, an amido, an amidino, a cyano, a nitro, an azido, a sulfonyl, a sulfoxido, a sulfate, a sulfonate, a sulfamoyl, a sulfonamido, a phosphoryl, a phosphonate, a phosphinate, $—(CH_2)_m—R8$, $—(CH_2)_m—OH$, $—(CH_2)_m—$O-lower alkyl, $—(CH_2)_m—$O-lower alkenyl, $—(CH_2)_m—$O$—(CH_2)_n—R8$, $—(CH_2)_m—SH$, $—(CH_2)_m—$S-lower alkyl, $—(CH_2)_m—$S-lower alkenyl, $—(CH_2)_m—$S$—(CH_2)_n—R8$, or protecting groups of the above or a solid or polymeric support; $R_8$ represents a substituted or unsubstituted aryl, aralkyl, cycloalkyl, cycloalkenyl, or heterocycle; and n and m are independently for each occurrence zero or an integer in the range of 1 to 6.

Metal-containing Catalysts

The catalysts employed in the subject method involve the use of metals which can mediate cross-coupling of the aryl groups ArX and Ar'YH as defined above. In general, catalysts intended by the present invention can be characterized in terms of a number of features. For instance, in preferred embodiments the metal should be capable of forming an adduct with the nucleophilic group of the reactive aryl in order to activate it for attack at an electrophilic center of the substrate aryl. For instance, a possible mechanism for the present reaction provides the metal catalyst in an intermediate form of an aryloxy adduct Ar'OM (where M is the metal).

In general, any transition metal (e.g., having d electrons) may be used to form the catalyst, e.g., a metal selected from one of Groups 3–12 of the periodic table or from the lanthanide series. However, in preferred embodiments, the metal will be selected from the group of late transition metals, e.g. preferably from Groups 5–12 and even more preferably Groups 7–11. For example, suitable metals include Cu, Co, Mn, Fe, and Ni. The particular form of the metal to be used in the reaction is selected to provide, under the reaction conditions, a metal center which is coordinately unsaturated and not in its highest oxidation state. Particularly preferred metals are copper, especially forms of the catalyst providing Cu(I) cations or which can be reduced or oxidized (as appropriate) to Cu(I) under the reaction conditions. For instance, Cu(I) can be produced by reaction between Cu(O) and Cu(II). For example, Jenkins et al. (1974) *J. Amer. Chem. Soc.*, 94:843 reports the preparation of cuprous triflate by the reaction of cupric triflate with copper metal in deoxygenated acetonitrile/triflic acid solution.

Without being bound by any particular theory, it is believed that the active copper species is Cu(I). However, by virtue of the oxidation-reduction processes occurring in the reaction mixture, the metal catalyst can be provided as its metallic form, as a metal salt, or as a metal oxide. However, the role of such factors as the solubility of the copper compound in the solvent system play a role in optimizing the selection of a copper catalyst.

In the case of metal salts, the counterion(s) can be selected from a variety of anion(s) of organic or inorganic origin, that can be, though not necessarily, weakly-nucleophilic (e.g., a weak base whose conjugate acid has a pKa less than 1). Weakly or non-nucleophilic stabilizing ions are preferred to avoid complicating side reactions of the counter ion involving attack at or addition to the electrophilic center of the substrate aryl.

Examples of suitable metal salts include those derived from arylsulfonic acids, alkylsulfonic acids, halogenated aryl- and alkylsulfonic acids, tetrafluoroboric acid, sulfuric acid, heteropolyacids, and halosulfonic acids. Sulfonic acid salts, especially triflate salts, are particularly preferred. For instance, suitable anions include fluorosulfate ($FSO_3^-$); alkyl sulfates, especially methyl sulfate ($CH_3SO_3^-$); perfluoroalkylsulfonates, such as triflate ($CF_3SO_3^-$) and nonaflate ($C_4F_9SO_3^-$); arenesulfonates, especially tosylate (i.e., p-toluenesulfonate; $CH_3C_6H_4SO_3^-$); alkylcarboxylates: perfluoroalkylcarboxylates; tetrafluoroborate ($BF_4^-$); tetraphenylborate ($Ph_4B^-$); hexafluorophosphate ($PF_6^-$); hexafluoroantimonate ($SbF_6^-$); chlorate ($ClO_3^-$); and sulfate ($SO_4^{-2}$).

To further illustrate, suitable inorganic copper ion sources include copper (II) triflate, copper tetrafluoroborate, copper p-toluenesulfonate, copper chloride, and the dihydrate thereof; copper fluoride, and the dihydrate thereof; copper fluorosilicate, and the hexahydrate thereof; copper sulphate, and the pentahydrate thereof; copper nitrate and the tri- and hexa-hydrates thereof; and also less popular copper salts, such as copper bromide; copper metaborate; copper bromate; copper chlorate; copper iodate; copper fluorophosphate, or mixtures thereof.

Preferred copper salts of organic acids include copper acetate, copper formate, copper benzoate, copper citrate, copper tartrate, copper lactate, copper malate, copper lysinate, copper mandelate, copper sorbate, copper pantothenate, copper gluconate, copper phytate, copper glycerophosphate, copper cinnamate, copper butyrate, copper propionate, copper laurate, copper oxalate, copper salicylate, copper glycinate, copper bis-glycinate or mixtures thereof. Mixtures of inorganic or organic salts may also be used.

It is understood, that the listed salts are only a small portion of the metal salts usable in the process. For the production of the catalysts of the invention, cost-effective inorganic salts are preferred.

Metallic copper can also be used, and can be obtained for use in the present method by, e.g., reducing $CuSO_4$ with zinc or by electrolytic deposition.

The preferred amount of catalyst to be used depends on many factors, including the catalyst type, reaction solvent, desired reaction rate, the type of substrate and reactive aryls used, reaction temperature, and other factors. Generally, it is preferred to use an amount of metal salt within the range of about 0.01% to 10 mol %.

Co-catalysts

In addition to the transition metal catalysts, the subject reaction preferably also includes a Lewis basic co-catalyst. While not wishing to be bound by any particular theory, experimental data supports the notion that the co-catalyst can be selected to be an agent having a functional group including an electron pair donor (Lewis base) capable of coordination with the transition metal. The co-catalyst may control the stability and electron transfer properties of the transition metal catalyst, and/or stabilize the metal intermediates.

Lewis basic moieties useful as a co-catalyst in this invention include linear and cyclic compounds which include at least one Lewis basic group. Such functionalities can be provided, in general, by such groups as ethers, esters, nitrites, ketones, amides, amines, phosphorus compounds and alcohols of up to 30 carbon atoms, and other organic Lewis bases which are soluble or can be suspended in the reaction mixture or solvent. Examples are alkyl and aryl acetates, alkyl acrylates, alkyl methacrylates, alkyl undecylenates, acetonitrile, benzonitrile, acrylonitrile, acetylacetone, tetrahydrofuran, pyridine, N,N-dimethylformamide, thiophene, ethyl ether, propyl ethers, diphenyl ether, triethylamine, phenylacetylene, organic phosphorus compounds of from 1 to 30 carbon atoms and monohydroxylic and dihydroxylicalcohols of from 1 to 30 carbon atoms such as methyl alcohol, ethyl alcohol, n-propyl alcohol, isopropyl alcohol, n-butyl alcohol, isobutyl alcohol, tert-butyl alcohol, n-pentyl alcohol, isopentyl alcohol, 2-methyl-1-butyl alcohol, 2-methyl-2-butyl alcohol, n-hexyl alcohol, n-heptyl alcohol, n-octyl alcohol, isooctyl alcohol, 2-ethylhexyl alcohol, n-nonyl alcohol, n-decyl alcohol, 1,5-aentanediol, 1,6-hexanediol, allyl alcohol, crotyl alcohol, 3-hexene-1-ol, citronellol, cyclopentanol, cyclohexanol, salicyl alcohol, benzyl alcohol, phenethyl alcohol, cinnamyl alcohol, and the like, and ketones, such as acetone, methyl ethyl ketone, diisopropyl ketone, benzophenone, acetophenone, dibenzyl ketone and the like.

The Lewis base is preferably an ester, such as an alkyl acetate, instead of an alcohol. A nitrile such as acetonitrile is preferable to pyridine.

As with the transition metal catalyst, the Lewis basic co-catalyst can be provided in the reaction mixture at sub-stoichiometric amounts. The preferred amount of co-catalyst to be used depends on many factors, including the catalyst type, reaction solvent, desired reaction rate, the type of substrate and reactive aryls used, reaction temperature, and other factors. Generally, it is preferred to use an amount of the Lewis base within the range of about 0.01% to 10 mol %.

Alkali or Alkaline Earth Salt

In one embodiment, the subject method is carried out in the presence of an inorganic salt selected from alkali metal salts and alkaline earth metal salts, in preferred embodiments the metal cation is characterized by having electrons in the $4^{th}$ or higher quantum level. The alkali salt, such as cesium carbonate, increases the solubility of the metal catalyst intermediates involving Ar'YH. The cationic portion is a "soft cation" (e.g., of large ionic radius) from the alkali metal or alkaline earth series, which cation can form an intermediate complex with a metal catalyst-activated Ar'YH.

For instance, the cation can be an alkali metal such as Rb, Cs and Fr, or an alkaline earth metal such as Sr, Ba and Ra. In many cases, the addition of such an alkali salt to the reaction mixture contributes to eliminating the need to form a phenoxide anion or the like prior to the condensation reaction, a salient feature of the reaction with respect to running the reaction in non-polar solvents.

Under certain of the reaction conditions, the anionic portion of the salt will preferably be a strong enough base to activate Ar'YH. For instance, where the reactive aryl is a phenol, the base portion of the salt should be strong enough to deprotonate the phenolic group. Therefore, for most reactions involving an arenol reactant, a base, the conjugate acid of which has a pKa of at least about 10, is required. For aryls groups such as anilines a stronger base may be needed, whereas for arylthiols a somewhat weaker base may be used.

In exemplary embodiments, the base can be: a carbonate of an alkali metal, e.g., cesium carbonate or cesium bicarbonate; an alkali or alkaline earth metal hydroxide; an alkali metal or alkaline earth metal alkoxides or amides, such as cesium methoxide, cesium ethoxide, or cesium tert-butoxide.

Acid Activator

Another aspect of the invention relates to the use of an acid activator, which as described above, is an acid selected to help solubilize key intermediates in the condensation reaction. In general, the activator will include an acidic group, e.g., with a pKa less than 5, capable of producing a conjugate base which, under the reaction conditions, is a strong enough Lewis base to donate an electron pair to the transition metal of the catalyst. Moreover, the activator will include substituents which generally render it, and its transition metal complexes, more soluble in the reaction solvent than the catalyst by itself. By use of such reaction additives, the resulting new procedure allows, for the first time, an efficient Ullmann reaction with less reactive and/or less soluble phenols.

In general, the acid activator is a compound that includes an anionic electron pair donor (Lewis basic) group which, though not being bound by a particular theory, is a potential ligand for metal catalyst complexes. To further illustrate, for example, suitable acid activators of the subject method include certain monofunctional or polyfunctional carboxylic acids, amides, hydroxamic acids, phosphoric acids, phosphonic acids, phosphinic acids, sulfonic acids, sulfinic acids, sulfenic acids, alkylboronic acids, arylboronic acids, silicic acids, alcohols, and thiols. In other embodiments, the acid activator includes a moiety which, under the reaction conditions, can be converted to a strongly acid group, such as an acid anhydride. In still other embodiments, the activator can be a phenol, e.g., a sterically crowded phenol. The electron donating compounds as described hereinabove may be used singly or in combination of two or more.

The acid activator can be used in the improved Ullmann reactions set out above, e.g., conjointly with an alkali salt such as cesium carbonate. Additionally, the acid activator can be used to improve the reaction for less reactive and/or less soluble phenols in the presence of a wide range of other bases, such as alkali salts generally.

In preferred embodiments, the acid activator is used in the subject reaction in the presence of molecular sieves such as zeolites. Zeolite molecular sieves are discussed in great detail in D. W. Breck, *Zeolite Molecular Sieves*, Robert E. Krieger Publishing Company, Malabar, Fla. (1984).

Reaction Conditions

The modified Ullmann reactions of the present invention may be performed under a wide range of conditions, though it will be understood that the solvents and temperature ranges recited herein are not limitative and only correspond to a preferred mode of the process of the invention.

In general, it will be desirable that reactions are run using mild conditions which will not adversely affect the reactants, the catalyst, or the product. For example, the reaction temperature influences the speed of the reaction, as well as the stability of the reactants and catalyst. The reactions will usually be run at temperatures in the range of 25° C. to 200° C., more preferably in the range 75° C. to 150° C.

In general, the subject reactions are carried out in a liquid reaction medium. However, the reactions may be run without addition of solvent. Alternatively, the reactions may be run in an inert solvent, preferably one in which the reaction ingredients, including the catalyst, are substantially soluble. Suitable solvents include ethers such as diethyl ether, 1,2-dimethoxyethane, diglyme, t-butyl methyl ether, tetrahydrofuran and the like; halogenated solvents such as chloroform, dichloromethane, dichloroethane, chlorobenzene, and the like; aliphatic or aromatic hydrocarbon solvents such as benzene, xylene, toluene, hexane, pentane and the like; esters and ketones such as ethyl acetate, acetone, and 2-butanone; polar aprotic solvents such as acetonitrile, dimethylsulfoxide, dimethylformamide and the like; or combinations of two or more solvents.

The invention also contemplates reaction in a biphasic mixture of solvents, in an emulsion or suspension, or reaction in a lipid vesicle or bilayer. In certain embodiments, it may be preferred to perform the catalyzed reactions on a solid phase, e.g., with one of the reactants anchored to a solid support.

In certain embodiments it is preferable to perform the reactions under an inert atmosphere of a gas such as nitrogen or argon.

The reaction processes of the present invention can be conducted in continuous, semi-continuous or batch fashion and may involve a liquid recycle operation as desired. The processes of this invention are preferably conducted in batch fashion. Likewise, the manner or order of addition of the reaction ingredients, catalyst and solvent are also not generally critical and may be accomplished in any conventional fashion.

The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the metal catalyst. When complete conversion is not desired or not obtainable, the starting materials can be separated from the product and then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

Furthermore, one or more of the reactants can be immobilized or incorporated into a polymer or other insoluble matrix by, for example, derivatization with one or more of substituents of the aryl group.

Combinatorial Libraries

The subject reactions readily lend themselves to the creation of combinatorial libraries of compounds for the screening of pharmaceutical, agrochemical or other biological or medically-related activity or material-related qualities. A combinatorial library for the purposes of the present invention is a mixture of chemically related compounds which may be screened together for a desired property; said libraries may be in solution or covalently linked to a solid support. The preparation of many related compounds in a single reaction greatly reduces and simplifies the number of screening processes which need to be carried out. Screening for the appropriate biological, pharmaceutical, agrochemical or physical property may be done by conventional methods.

Diversity in a library can be created at a variety of different levels. For instance, the substrate aryl groups used in a combinatorial approach can be diverse in terms of the core aryl moiety, e.g., a variegation in terms of the ring structure, and/or can be varied with respect to the other substituents.

A variety of techniques are available in the art for generating combinatorial libraries of small organic molecules. See, for example, Blondelle et al. (1995) Trends Anal. Chem. 14:83; the Affymax U.S. Pat. Nos. 5,359,115 and 5,362,899: the Ellman U.S. Pat. No. 5,288,514: the Still et al. PCT publication WO 94/08051; Chen et al. (1994) JACS 116:2661: Kerr et al. (1993) JACS 115:252; PCT publications WO92/10092, WO93/09668 and WO091/07087; and the Lerner et al. PCT publication WO93/20242). Accordingly, a variety of libraries on the order of about 16 to 1,000,000 or more diversomers can be synthesized and screened for a particular activity or property.

In an exemplary embodiment, a library of substituted diversomers can be synthesized using the subject reactions adapted to the techniques described in the Still et al. PCT publication WO 94/08051, e.g., being linked to a polymer bead by a hydrolyzable or photolyzable group, e.g., located at one of the positions of substrate. According to the Still et al. technique, the library is synthesized on a set of beads, each bead including a set of tags identifying the particular diversomer on that bead. In one embodiment, which is particularly suitable for discovering enzyme inhibitors, the beads can be dispersed on the surface of a permeable membrane, and the diversomers released from the beads by lysis of the bead linker. The diversomer from each bead will diffuse across the membrane to an assay zone, where it will interact with an enzyme assay. Detailed descriptions of a number of combinatorial methodologies are provided below.

Direct Characterization

A growing trend in the field of combinatorial chemistry is to exploit the sensitivity of techniques such as mass spectrometry (MS), e.g., which can be used to characterize sub-femtomolar amounts of a compound, and to directly determine the chemical constitution of a compound selected from a combinatorial library. For instance, where the library is provided on an insoluble support matrix, discrete populations of compounds can be first released from the support and characterized by MS. In other embodiments, as part of the MS sample preparation technique, such MS techniques as MALDI can be used to release a compound from the matrix, particularly where a labile bond is used originally to tether the compound to the matrix. For instance, a bead selected from a library can be irradiated in a MALDI step in order to release the diversomer from the matrix, and ionize the diversomer for MS analysis.

B) Multipin Synthesis

The libraries of the subject method can take the multipin library format. Briefly, Geysen and co-workers (Geysen et al. (1984) PNAS 81:3998–4002) introduced a method for generating compound libraries by a parallel synthesis on polyacrylic acid-grated polyethylene pins arrayed in the microtitre plate format. The Geysen technique can be used to synthesize and screen thousands of compounds per week using the multipin method, and the tethered compounds may be reused in many assays. Appropriate linker moieties can also been appended to the pins so that the compounds may be cleaved from the supports after synthesis for assessment of purity and further evaluation (c.f., Bray et al. (1990) Tetrahedron Lett 31:5811–5814; Valerio et al. (1991) Anal Biochem 197:168–177; Bray et al. (1991) Tetrahedron Lett 32:6163–6166).

C) Divide-Couple-Recombine

In yet another embodiment, a variegated library of compounds can be provided on a set of beads utilizing the strategy of divide-couple-recombine (see, e.g., Houghten (1985) PNAS 82:5131–5135; and U.S. Pat. Nos. 4,631,211; 5,440,016; 5,480,971). Briefly, as the name implies, at each synthesis step where degeneracy is introduced into the library, the beads are divided into separate groups equal to the number of different substituents to be added at a particular position in the library, the different substituents coupled in separate reactions, and the beads recombined into one pool for the next iteration.

In one embodiment, the divide-couple-recombine strategy can be carried out using an analogous approach to the so-called "tea bag" method first developed by Houghten, where compound synthesis occurs on resin sealed inside porous polypropylene bags (Houghten et al. (1986) PNAS 82:5131–5135). Substituents are coupled to the compound-bearing resins by placing the bags in appropriate reaction solutions, while all common steps such as resin washing and deprotection are performed simultaneously in one reaction vessel. At the end of the synthesis, each bag contains a single compound.

D) Combinatorial Libraries by Light-Directed, Spatially Addressable Parallel Chemical Synthesis A scheme of combinatorial synthesis in which the identity of a compound is given by its locations on a synthesis substrate is termed a spatially-addressable synthesis. In one embodiment, the combinatorial process is carried out by controlling the addition of a chemical reagent to specific locations on a solid support (Dower et al. (1991) Annu Rep Med Chem 26:271–280; Fodor, S. P. A. (1991) Science 251:767; Pirrung et al. (1992) U.S. Pat. No. 5,143,854; Jacobs et al. (1994) Trends Biotechnol 12:19–26). The spatial resolution of photolithography affords miniaturization. This technique can be carried out through the use protection/deprotection reactions with photolabile protecting groups.

The key points of this technology are illustrated in Gallop et al. (1994) J Med Chem 37:1233–1251. A synthesis substrate is prepared for coupling through the covalent attachment of photolabile nitroveratryloxycarbonyl (NVOC) protected amino linkers or other photolabile linkers. Light is used to selectively activate a specified region of the synthesis support for coupling. Removal of the photolabile protecting groups by light (deprotection) results in activation of selected areas. After activation, the first of a set of amino acid analogs, each bearing a photolabile protecting group on the amino terminus, is exposed to the entire surface. Coupling only occurs in regions that were addressed by light in the preceding step. The reaction is stopped, the plates washed, and the substrate is again illuminated through a second mask, activating a different region for reaction with a second protected building block. The pattern of masks and the sequence of reactants define the products and their locations. Since this process utilizes photolithography techniques, the number of compounds that can be synthesized is limited only by the number of synthesis sites that can be addressed with appropriate resolution. The position of each compound is precisely known; hence, its interactions with other molecules can be directly assessed.

In a light-directed chemical synthesis, the products depend on the pattern of illumination and on the order of addition of reactants. By varying the lithographic patterns, many different sets of test compounds can be synthesized simultaneously; this characteristic leads to the generation of many different masking strategies.

E) Encoded Combinatorial Libraries

In yet another embodiment, the subject method utilizes a compound library provided with an encoded tagging system. A recent improvement in the identification of active compounds from combinatorial libraries employs chemical indexing systems using tags that uniquely encode the reaction steps a given bead has undergone and, by inference, the structure it carries. Conceptually, this approach mimics phage display libraries, where activity derives from expressed peptides, but the structures of the active peptides are deduced from the corresponding genomic DNA sequence. The first encoding of synthetic combinatorial libraries employed DNA as the code. A variety of other forms of encoding have been reported, including encoding with sequenceable bio-oligomers (e.g., oligonucleotides and peptides), and binary encoding with additional non-sequenceable tags.

1) Tagging with sequenceable bio-oligomers

The principle of using oligonucleotides to encode combinatorial synthetic libraries was described in 1992 (Brenner et al. (1992) PNAS 89:5381–5383), and an example of such a library appeared the following year (Needles et al. (1993) PNAS 90:10700–10704). A combinatorial library of nominally $7^7$ (=823,543) peptides composed of all combinations of Arg, Gln, Phe, Lys, Val, D-Val and Thr (three-letter amino acid code), each of which was encoded by a specific dinucleotide (TA, TC, CT, AT, TT, CA and AC, respectively), was prepared by a series of alternating rounds of peptide and oligonucleotide synthesis on solid support. In this work, the amine linking functionality on the bead was specifically differentiated toward peptide or oligonucleotide synthesis by simultaneously preincubating the beads with reagents that generate protected OH groups for oligonucleotide synthesis and protected $NH_2$ groups for peptide synthesis (here, in a ratio of 1:20). When complete, the tags each consisted of 69-mers, 14 units of which carried the code. The bead-bound library was incubated with a fluorescently labeled antibody, and beads containing bound antibody that fluoresced strongly were harvested by fluorescence-activated cell sorting (FACS). The DNA tags were amplified by PCR and sequenced, and the predicted peptides were synthesized. Following such techniques, compound libraries can be derived for use in the subject method, where the oligonucleotide sequence of the tag identifies the sequential combinatorial reactions that a particular bead underwent, and therefore provides the identity of the compound on the bead.

The use of oligonucleotide tags permits exquisitely sensitive tag analysis. Even so, the method requires careful choice of orthogonal sets of protecting groups required for alternating co-synthesis of the tag and the library member. Furthermore, the chemical lability of the tag, particularly the phosphate and sugar anomeric linkages, may limit the choice of reagents and conditions that can be employed for the synthesis of non-oligomeric libraries. In preferred embodiments, the libraries employ linkers permitting selective detachment of the test compound library member for assay.

Peptides have also been employed as tagging molecules for combinatorial libraries. Two exemplary approaches are described in the art, both of which employ branched linkers to solid phase upon which coding and ligand strands are alternately elaborated. In the first approach (Kerr JM et al. (1993) J Am Chem Soc 115 :2529–2531), orthogonality in synthesis is achieved by employing acid-labile protection for the coding strand and base-labile protection for the compound strand.

In an alternative approach (Nikolaiev et al. (1993) Pept Res 6:161–170), branched linkers are employed so that the coding unit and the test compound can both be attached to the same functional group on the resin. In one embodiment, a cleavable linker can be placed between the branch point and the bead so that cleavage releases a molecule containing both code and the compound (Ptek et al. (1991) Tetrahedron Lett 32:3891–3894). In another embodiment, the cleavable linker can be placed so that the test compound can be selectively separated from the bead, leaving the code behind. This last construct is particularly valuable because it permits screening of the test compound without potential interference of the coding groups. Examples in the art of independent cleavage and sequencing of peptide library members and their corresponding tags has confirmed that the tags can accurately predict the peptide structure.

2) Non-sequenceable Tagging: Binary Encoding

An alternative form of encoding the test compound library employs a set of non-sequencable electrophoric tagging molecules that are used as a binary code (Ohlmeyer et al. (1993) PNAS 90:10922–10926). Exemplary tags are haloaromatic alkyl ethers that are detectable as their trimethylsilyl ethers at less than femtomolar levels by electron capture gas chromatography (ECGC). Variations in the length of the alkyl chain, as well as the nature and position of the aromatic halide substituents, permit the synthesis of at least 40 such tags, which in principle can encode $2^{40}$ (e.g., upwards of $10^{12}$) different molecules. In the original report (Ohlmeyer et al., supra) the tags were bound to about 1% of the available amine groups of a peptide library via a photocleavable o-nitrobenzyl linker. This approach is convenient when preparing combinatorial libraries of peptide-like or other amine-containing molecules. A more versatile system has, however, been developed that permits encoding of essentially any combinatorial library. Here, the compound would be attached to the solid support via the photocleavable linker and the tag is attached through a catechol ether linker via carbene insertion into the bead matrix (Nestler et al. (1994) J Org Chem 59:4723–4724). This orthogonal attachment strategy permits the selective detachment of library members for assay in solution and subsequent decoding by ECGC after oxidative detachment of the tag sets.

Although several amide-linked libraries in the art employ binary encoding with the electrophoric tags attached to amine groups, attaching these tags directly to the bead matrix provides far greater versatility in the structures that can be prepared in encoded combinatorial libraries. Attached in this way, the tags and their linker are nearly as unreactive as the bead matrix itself. Two binary-encoded combinatorial libraries have been reported where the electrophoric tags are attached directly to the solid phase (Ohlmeyer et al. (1995) PNAS 92:6027–6031) and provide guidance for generating the subject compound library. Both libraries were constructed using an orthogonal attachment strategy in which the library member was linked to the solid support by a photolabile linker and the tags were attached through a linker cleavable only by vigorous oxidation. Because the library members can be repetitively partially photoeluted from the solid support, library members can be utilized in multiple assays. Successive photoelution also permits a very high throughput iterative screening strategy: first, multiple beads are placed in 96-well microtiter plates; second, compounds are partially detached and transferred to assay plates; third, a metal binding assay identifies the active wells; fourth, the corresponding beads are rearrayed singly into new microtiter plates; fifth, single active compounds are identified; and sixth, the structures are decoded.

EXEMPLIFICATION

The invention now being generally described, it will be more readily understood by reference to the following examples which are included merely for purposes of illustration of certain aspects and embodiments of the present invention, and are not intended to limit the invention.

EXAMPLE 1
Improved Reaction Conditions for the Ullmann Biphenylether Synthesis.

The first general procedure for the copper-catalyzed Ullmann reaction of a wide range of activated and unactivated aryl bromides and iodides with phenols is described. It has been found that the use of cesium carbonate as a base allows the reaction to proceed in toluene at 110° C. and gives access to the corresponding diaryl ethers in good to excellent yields with a high level of functional group tolerance. The use of 1-naphthoic acid as an additive extends the applicability of this procedure to less soluble phenols and phenols containing electron-withdrawing groups.

Diaryl ethers are useful intermediates in organic synthesist and are found in a large number of biologically active compounds[1-8] including K13,[3] OF 4949 I–IV,[4] bouvardin,[5] deoxybouvardin,[5] RA I–VII,[6] vancomycin[7] and recently reported HIV-protease inhibitors.[8] A key step in many of these syntheses is the formation of a diaryl ether via an intra- or intermolecular coupling of a phenol and an aryl halide.[9] The Ullmann ether synthesis[10] has been extensively used and has found numerous applications since its discovery in the beginning of this century.[11,12] However, the harsh reaction conditions (125–220° C. in neat phenol or solvents such as pyridine, collidine or DMF), the usual requirement for stoichiometric (or greater) quantities of the copper complex, and the fact that unactivated aryl halides usually react in low yields have limited the utility of this reaction. Recent efforts to develop procedures which are applicable to more complex synthetic intermediates have met with only limited success[12a, 13] or require the use of an activating group.[14]

We now report a mild and general procedure for the formation of diaryl ethers from the reaction of aryl bromides and iodides with a variety of phenols (Scheme 1). The new procedure is characterized by the following features: a) its use of a catalytic amount of a copper complex (0.05 to 2.5 mol %), b) its use of cesium carbonate as a base, which eliminates the need to form the phenoxide anion prior to the reaction, c) its ability to employ a non-polar solvent (toluene) and lower reaction temperatures than previous reactions, and d) its use of a stoichiometric amount of a carboxylic acid in the reactions of unactivated aryl halides with less soluble phenols and phenols containing electron-withdrawing groups.

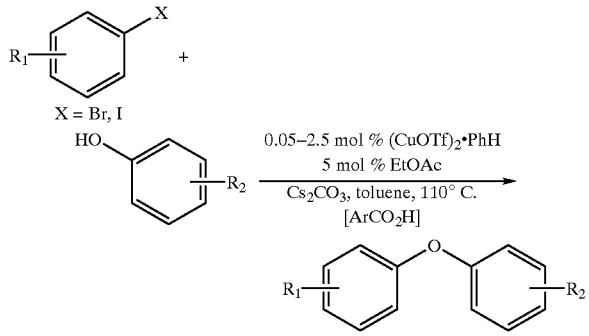

Scheme 1

During a study directed toward finding new methods for the preparation of diaryl ethers, we discovered that the reaction of 3,4-dimethylphenol with tert-butylbromobenzene using a catalytic amount of a copper complex and cesium carbonate as base in DMF at 110° C. gave the desired diaryl ether product in >80% yield. These reaction conditions proved to be surprisingly efficient for this reaction with an unactivated aryl bromide substrate. Examination of the reaction parameters showed that the conversion and the rate of the reaction were highly dependent on the base used. For example, the use of potassium carbonate, which is known to be an effective base for certain Ullmann couplings in DMF and other polar solvents,[11] gave <35% yield for the same reaction. To the best of our knowledge, the use of cesium carbonate for the Ullmann diaryl ether synthesis has never been reported. The higher reactivity obtained with cesium carbonate prompted us to try the reaction in less polar solvents such as THF, ethyl acetate and toluene in order to avoid the problems associated with the use of toxic, high-boiling or water-soluble solvents such as DMF and pyridine. Toluene was found to be the most effective solvent, giving $>$70% yield after 24 h at 100° C. As previously reported for the copper-catalyzed methoxylation of aryl bromides, the addition of a catalytic amount of ethyl acetate (5 mol %) resulted in a faster reaction[15] and in $>$90% conversion in less than 20 h.[6] A survey of reactions using a number of other bases ($Et_3N$, DIPEA, DBU, 1,2,2,6,6-pentamethylpiperidine, dicyclohexylmethylamine), including other carbonates, such as $K_2CO_3$, $Li_2CO_3$, $Na_2CO_3$ and $BaCO_3$, gave only trace amounts of the desired product and confirmed that cesium carbonate is a key element responsible for the improved reaction conditions. The choice of the copper catalyst did not appear to be critical; CuCl, CuBr, CuI, $CuBr_2$, $CuSO_4$ gave similar results. However, we found that the use of $(CuOTf)_2$. benzene led to slightly accelerated reaction rates, particularly during the beginning of the reaction. We speculate that the higher solubility of $(CuOTf)_2$. benzene in toluene, compared to other copper salts, increases the rate of formation of the reactive copper catalyst. A slight excess of the phenol was used (0.4–1.0 equiv excess) since the use of 1.0 equiv resulted in very slow conversion as the reaction neared completion.

As shown in Table 1, the procedure employing cesium carbonate as base is extremely effective in coupling phenols with both activated and unactivated aryl bromides and iodides. Consistent with previous studies, aryl iodides react faster than aryl bromides, and aryl chlorides are unreactive.[11,17–18] The mild reaction conditions are compatible with a wide range of functionalized substrates, including those containing ethers, ketones, carboxylic acids, esters, dialkylamines, nitriles, nitro groups[18] and aryl chlorides, whereas those containing amides were found to be poor substrates. This method is particularly suitable for unactivated aryl halides and ortho-substituted phenols; e.g., coupling of the sterically demanding 2-isopropylphenol with 2-iodo-p-xylene proceeds in high yield (entry 15). Reactions employing 2,6-dimethylphenol were inefficient and reductive homocoupling of the 5-iodo-m-xylene was the major reaction observed (entry 13). Surprisingly, p-cresol was less reactive than o-cresol or 3,4-dimethylphenol (entries 8–10, 16), and the use of phenol or p-chlorophenol produced only small amounts of the desired ethers (entries 18,20). In these cases, we surmised that the lower solubility of the corresponding cesium phenolate or of the phenoxide-copper complex may account for the lack of reactivity. In order to circumvent this limitation, we investigated the use of different additives that could help solubilize the key intermediates. We found that stoichiometric quantities of certain carboxylic acids,[19] particularly 1-naphthoic acid, in the presence of molecular sieves[20] promoted the reaction of less reactive phenols. The resulting new procedure allowed for the first time the successful Ullmann coupling of unactivated aryl halides and less reactive phenols, such as phenol and chlorophenol (entries 18,20).[21] The good yield obtained for the coupling of p-cresol and 2-bromoanisole (entry 16) is also noteworthy compared with the 44% reported by Boger for the same product using the more reactive iodide in the presence of an excess of sodium hydride and of CuBr (2.0 equiv).[13b] Furthermore, the fact that the use of a catalyst level as low as 0.05 mol % of $(CuOTf)_2$. benzene resulted in only a slight decrease in yield (entries 1,3,20) suggests that the reaction conditions are sufficiently mild to prevent the undesired reduction of copper(I) species to copper(0); this process has been reported to occur in more strongly coordinating solvents, thereby decreasing the amount of reactive copper complex available in the reaction mixture.[22]

TABLE 1

Copper(I) triflate-catalyzed formation of diaryl ethers in toluene in the presence of cesium carbonate.

| Entry | Halide | Phenol | Aryl ether | Equiv of phenol | Isolated yield without additive (%)[a] | Isolated yield with additive (%)[b] |
|---|---|---|---|---|---|---|
| 1 | X = I | R = Cl | | 1.4 | 89 (87)[c] | |
| 2 | Br | COOEt | | 1.4 | 81[d] | |
| 3 | I | Me | | 1.4 | 87 (86)[c] (72)[e] | |
| 4 | Br | t-Bu | | 1.4 | 85 | |
| 5 | I | t-Bu | | 1.4 | 91 | |
| 6 | I | OMe | | 1.4 | 77 | |
| 7 | Br | $NMe_2$ | | 1.4 | 83 | |
| 8 | (3,5-dimethyl-iodobenzene) | (4-OH-3,4-dimethylphenol) | (aryl ether) | 1.4 | 90 | |
| 9 | (3,5-dimethyl-iodobenzene) | (o-cresol) | (aryl ether) | 1.4 | 87 | |
| 10 | (3,5-dimethyl-iodobenzene) | (p-cresol) | (aryl ether) | 1.4 | 29 | 80 |
| 11 | (2,4-dimethyl-iodobenzene) | (o-cresol) | (aryl ether) | 2.0 | 85 | |

TABLE 1-continued

Copper(I) triflate-catalyzed formation of diaryl ethers in toluene in the presence of cesium carbonate.

| Entry | Halide | Phenol | Aryl ether | Equiv of phenol | Isolated yield without additive (%)[a] | Isolated yield with additive (%)[b] |
|---|---|---|---|---|---|---|
| 12 | 2-Br-C6H4-CO2H | 3,4-dimethylphenol | 2-(3,4-dimethylphenoxy)benzoic acid | 2.0 | 84 | |
| 13 | 3,5-dimethyl-iodobenzene | 2,6-dimethylphenol | 3,5-dimethylphenyl 2,6-dimethylphenyl ether | 2.0 | 20–30[f] | |
| 14 | 4-iodotoluene | 2-isopropylphenol | 4-methylphenyl 2-isopropylphenyl ether | 1.4 | 76 | |
| 15 | 2-iodo-p-xylene | 2-isopropylphenol | 2,5-dimethylphenyl 2-isopropylphenyl ether | 1.4 | 83 | |
| 16 | 2-bromoanisole | 4-methylphenol | 2-methoxyphenyl 4-methylphenyl ether | 2.0 | 5[g] | 79 |
| 17 | 4-bromobenzonitrile | phenol | 4-cyanophenyl phenyl ether | 2.0 | 88 | |

TABLE 1-continued

Copper(I) triflate-catalyzed formation of diaryl ethers in toluene in the presence of cesium carbonate.

| Entry | Halide | Phenol | Aryl ether | Equiv of phenol | Isolated yield without additive (%)[a] | Isolated yield with additive (%)[b] |
|---|---|---|---|---|---|---|
| 18 | 4-t-Bu-C6H4-Br | PhOH | 4-t-Bu-C6H4-O-Ph | 1.4 | 0[g] | 81 |
| 19 | 4-MeC(O)-C6H4-I | 4-Cl-C6H4-OH | 4-MeC(O)-C6H4-O-C6H4-4-Cl | 2.0 | | 93 |
| 20 | 4-Me-C6H4-I | 4-Cl-C6H4-OH | 4-Me-C6H4-O-C6H4-4-Cl | 2.0 | 34[g] | 79 (69)[d] |

1H NMR, and elemental analysis.
[a]All the reactions were conducted in toluene at 110 C. in the presence of 1.4 or 2.0 equiv of Cs2CO3, 2.5 mol % of (CuOTf)2 PhH (5 mol % Cu) and 5 mol % of EtOAc for 12–26 h;
[b]An equimolar amount of 1-naphtoic acid (compared to the cesium carbonate) and 250 mg/mmol of activated 5A MS were added to the mixture;
[c]0.25 mol % of (CuOTf)2 PhH was used;
[d]0.05 mol % of (CuOTf)2 PhH was used;
[e]Yield obtained with p-tert-butyllodobenzene;
[f]approximative yield because the product was contaminated with ca. 25% of a by-product resulting from the reductive homocoupling of the aryl iodide;
[g]GC yields;
[h]Only one experiment was conducted.

It has been proposed that copper-catalyzed nucleophilic substitution proceeds via the formation of a complex between the aryl halide and the copper.[11] As previously reported,[11,23] we observed that the rate of the reaction was not greatly influenced by the presence of electron-donating or electron-withdrawing groups on the aryl halide or phenol substrates (in the latter case, this refers to reactions in the presence of 1-naphthoic acid). This observation, combined with the fact that aryl triflates and unactivated aryl chlorides failed to react, does not support a mechanism in which a negative charge develops on the aromatic ring resulting from the direct attack of the phenolate.[11b] It has recently been proposed that the methoxylation of aryl bromides involves the formation of an active cuprate-like intermediate of the general structure $[(RO)_2Cu]^-M^+$.[22,24] We believe that the nature of the cation plays an important role during the formation or the solubilization of such an intermediate. Cesium phenoxides and carboxylates are relatively soluble in organic solvents.[25] Their use could enhance the solubility of the possible key reaction intermediates 1 and 2 (Scheme 2), as compared to their potassium and sodium counterparts. Evidence suggests that the 1-naphthoic acid plays an active role during the reaction and is not simply functioning as an acidic additive.[26] Based on the recent report,[19] we suggest that in the presence of less nucleophilic phenols, the cesium naphthoate participates in the formation of the reactive intermediate 2, thereby increasing its solubility and the rate of its subsequent reaction.[27,28]

Scheme 2

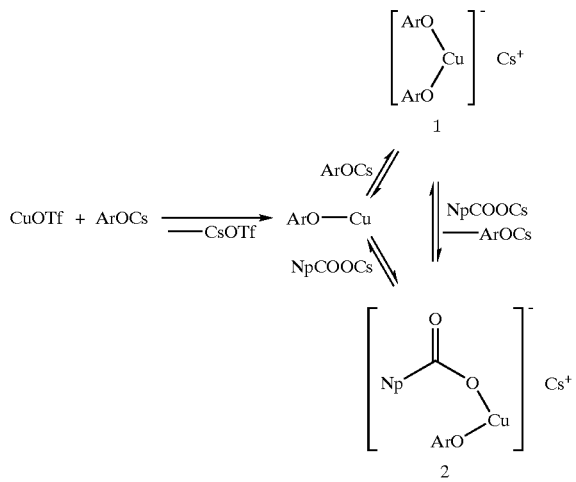

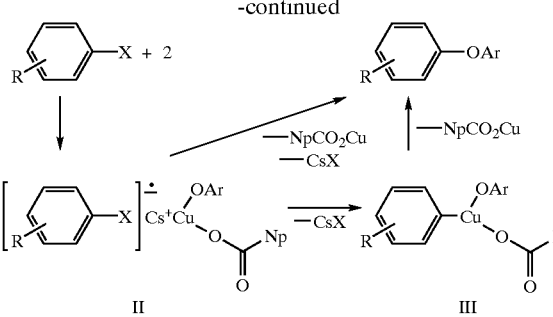

In summary, we have developed the first general procedure for the copper-catalyzed coupling of a wide range of activated and unactivated aryl bromides and iodides with phenols, using cesium carbonate as a base. In addition, the use of 1-naphthoic acid as an additive for the efficient coupling of less soluble phenoxides is important in that it extends the generality of the reaction, rendering it more useful in organic synthesis. Moreover, this finding opens the way to the development of new copper catalysts for related transformations. Mechanistic investigations on the role of the cation and of the carboxylic acid additives and the application of this methodology are also contemplated.

References and Footnotes for Example 1

(1) Pellón, R. F.; Carrasco, R.; Milián, V.; Rodes, L. *Synth. Commun.* 1995, 25, 1077 and references cited therein.
(2) For recent reviews on natural biphenyl ether peptides, see: (a) Evans, D. A.; DeVries, K. M. In *Glycopeptide Antibiotics, Drugs and the Pharmaceutical Sciences*; Nagarajan, R., Ed.; Marcel Decker, Inc.: New York, 1994; Vol. 63, pp. 63–104. (b) Itokama, H.; Takeya, K. *Heterocycles* 1993, 35, 1467.
(3) Kase, H.; Masami, K.; Yamada, K. *J. Antibiot.* 1987, 40, 450.
(4) (a) Sano, S.; Ikai, K.; Kuroda, H.; Nakamura, T.; Obayashi, A.; Ezure, Y.; Enomoto, H. *J. Antibiot.* 1986, 39, 1674. (b) Sano, S.; Ikai, K.; Katayama, K.; Takesako, K.; Nakamura, T.; Obayashi, A.; Ezure, Y.; Enomoto, H. *J. Antibiot.* 1986, 39, 1685.
(5) Jolad, S. D.; Hoffmann, J. J.; Torrance, S. J.; Wiedhopf, R. M.; Cole, J. R.; Arora, S. K.; Bates, R. B.; Gargiulo, R. L.; Kriek, G. R. *J. Am. Chem. Soc.* 1977, 99, 8040.
(6) (a) Itokawa, H.; Takeya, K.; Mihara, K.; Noboru, M.; Hamanaka, T.; Sonobe, T.; Iitaka, Y. *Chem. Pharm. Bull.* 1983, 31, 1424. (b) Itokawa, H.; Takeya, K.; Mori, N.; Hamanaka, T.; Sonobe, T.; Mihara, K. *Chem. Pharm. Bull.* 1984, 32, 284.
(7) Williams, D. H. *Acc. Chem. Res.* 1984, 17, 364.
(8) (a) Janetka, J. W.; Raman, P.; Satyshur, K.; Flentke, G. R., Rich, D. H. *J. Am. Chem. Soc.* 1997, 119, 441. (b) Pearson, A. J.; Bignan, G.; Zhang, P.; Chelliah, M. *J. Org. Chem.* 1996, 61, 3940.
(9) Selected examples: (a) Nucleophilic substitution of aryl fluorides: Beugelmans, R.; Bigot, A.; Zhu, J. *Tetrahedron Lett.* 1994, 35, 5649. (b) Ruthenium [1]-arene complexes: Janetka, J. W.; Rich, D. H. *J. Am. Chem. Soc.* 1995, 117, 10585, and ref. 8b.
(10) Ullmann, F. *Chem. Ber.* 1904, 37, 853.
(11) General reviews: (a) Moroz, A. A.; Shvartsberg, M. S. *Russ. Chem. Rev.* 1974, 43, 679. (b) Lindley, J. *Tetrahedron* 1984, 40, 1433.
(12) (a) Evans, D. A.; Ellman, J. A. *J. Am. Chem. Soc.* 1989, 111, 1063. (b) Boger, D. L.; Yohannes, D. *J. Org. Chem.* 1990, 55, 6000. (c) Boger, D. L.; Patane, M. A.; Zhou, J. *J. Am. Chem. Soc.* 1994, 116, 8544. (d) Carruthers, W. in *Comprehensive Organometallic Chemistry*, Wilkinson, G., Ed.; Pergamon Press, 1982, Vol. 7, p 690
(13) (a) Boger, D. L.; Sakya, S. M.; Yohannes, D. *J. Org. Chem.* 1991, 56, 4204. (b) Boger, D. L.; Yohannes, D. *Tetrahedron Lett.* 1989, 30, 2053. (c) Jung, M. E.; Jachiet, D.; Rohloff, J. C. *Tetrahedron Lett.* 1989, 30, 4211. (d) Nogradi, M.; Vermes, B., Kajiar-Peredy, M. *Tetrahedron Lett.* 1987, 28, 2899. (e) Tomita, M.; Fujitami, K.; Aoyagi, Y. *Chem. Pharm. Bull.* 1965, 13, 1341.
(14) For selected examples with ortho-activating groups, see: (a) Nicolaou, K. C.; Boddy, C. N. C.; Natarajan, S.; Yue, T.-Y.; Li, H.; Bräse, S.; Ramanjulu, J. M. *J Am. Chem. Soc.* 1997, 119, 3421. (b) Rozanel'skaya, N. A.; Stepanov, B. I. *Zhur. Obshch, Khim.* 1961, 31, 758. (c) ref. 1.
(15) The formation of a more soluble copper(I) complexes, resulting from the formation of an adduct between the added ester and the alkoxide have been proposed to be responsible for the rate enhancement. Capdevielle, P.; Maumy, M. *Tetrahedron Lett.* 1993, 34, 1007.
(16) Addition of more than 5 mol % of ethyl acetate resulted in lower conversions.
(17) Weingarten, H. *J. Org. Chem.* 1964, 29, 977.
(18) Highly activated aryl chlorides, such as o-nitrochlorobenzene, reacted under these conditions, but in this case the uncatalyzed process is also possible.
(19) 2-thiophenecarboxylic acid has been reported to enhance the reductive homocoupling of aryl iodides: Zhang, S.; Zhang, D.; Liebeskind, L. S. *J. Org. Chem.* 1997, 62, 2312.
(20) The reaction between 1-naphthoic acid and cesium carbonate leads to the formation of some water. The addition of 5 Å molecular sieves increases the rate of the reaction by removing the water thus formed.
(21) Whereas a few successful examples of Ullmann couplings between electron-deficient phenols and activated aryl halides have been reported (ref. 11), to the best of our knowledge no general study concerning the use of unactivated aryl halides has appeared in the literature.
(22) Aalten, H. L.; van Koten, G.; Grove, D. M.; Kuilman, T.; Piekstra, O. G.; Hulshof, L. A.; Sheldon, R. A. *Tetrahedron* 1989, 45, 5565.
(23) Lituak, V. V.; Shein, S. M. *Zh. Org Khim.* 1974, 10, 550. Eng. Ed. 1974, 2373.
(24) van Koten et. al. (ref. 22) also suggest that the cuprate-like copper complex $M^+[(RO)_2Cu]^-$ is in equilibrium with the unreactive dimer $[M+[(RO)_2Cu]^-]_2$. The nature of the cation could also have an effect on this equilibrium, thereby affecting the rate and the extent of the reaction.
(25) (a) Hennings, D. D.; Imasa, S.; Rawal, V. R. *J. Org. Chem.* 1997, 62, 2. (b) Kwizinga, W. H.; Kellogg, R. M. *J. Chem. Soc., Chem. Commun.* 1979, 286. (c) Zaugg, H. E. *J. Org. Chem.* 1976, 41, 3419.
(26) For the reaction shown in entry 18, the addition of preformed cesium naphthoate to a mixture containing preformed cesium phenolate, 1-bromo-4-tert-butylbenzene, and 2.5 mol % of $(CuOTf)_2$. PhH allowed the reaction to occur.
(27) The use of greater quantity of catalyst did not result in an increase in the rate of or the extent of conversion of the reaction, suggesting that the solubility of the reactive copper complex is very low under the conditions employed.
(28) The mechanism of the formation of the aryl ether is unclear. Based on other reports (ref. 22, 23), we believe that the reaction could involve an initial electron transfer to the aryl halide, followed by the formation of the diaryl

EXAMPLE 2
Improved Reaction Conditions for the Ullmann Biphenylether Synthesis Biphenyl ethers are useful intermediates in organic synthesis[1] and are found in an ever-increasing number of biologically active natural products.[1-8] An Important class of these natural products are cyclic piphenyl ether peptides[2] such as K13 (inhibitor of Angiotensin I),[3] OF4949 I–IV (inhibitors of aminopeptidase B),[4] Bouvardin,[5] Deoxybouvardin[5] and RA I–VII (antitumor antibiotics),[6] the Vancomycin group of antibiotics[7] and some recently reported HIV-protease inhibitors.[8]

Since the beginning of the century the classical Ullmann biphenyl ether synthesis[9] has been extensively used for preparation of aryl ethers.[10] The conditions used for the copper catalyzed coupling of aryl halides and phenols are usually harsh and require temperatures between 125–220° C.[10] Moreover high boiling and polar solvents (pyridine, collidine, DMF) and stoichiometric amounts of copper are often needed. the phenol can be used as its preformed sodium-, potassium- or copper-salt or can be deprotonated in situ with a base (NaH, $K_2CO_3$, $Na_2CO_3$.[10] The yields are very substrate-dependent and are usually low for transformations including highly functionalized substrates. For example, during the course of the total synthesis of the antibiotics mentioned above, all attempts using Ullmann conditions for the coupling of advanced intermediates were unsuccessful.

Herein we report very mild conditions for the coupling of various aryl bromides and iodides with a number of phenols. Surprisingly, the reaction proceeds in toluene at 110° C. with 5 mol % of a copper salt when $Cs_2CO_3$ is used as a base. The reaction times are normally between 12 and 25 hours. The yields are usually high. We also found that a stoichiometric amount of some carboxylic acids as an additive, particularly 1-naphthoic acid, dramatically increases conversion and the yield for the coupling of less reactive phenols. In this case, $K_2CO_3$ can also be used as a base.

Scheme 1

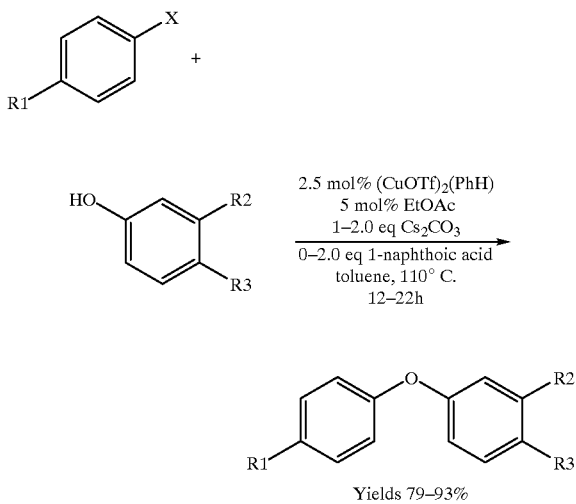

X = Br, I
R1 = Me, t-Bu, OMe, C(O)Me, Cl, CN
R2 = H, Me
R3 = H, Me, Cl

Scheme 2

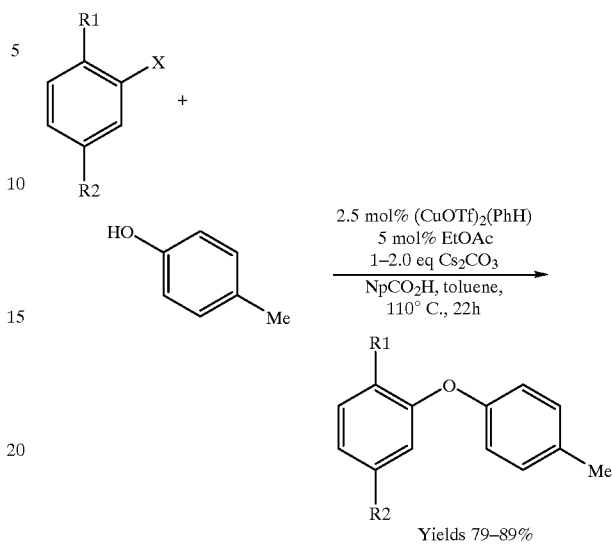

X = Br, I
R1 = Me, OMe,
R2 = Me, H

To our knowledge there are no comparable mild reaction conditions known for such a copper-catalyzed biphenyl ether synthesis. The use of $Cs_2CO_3$ as a base, which is necessary for the reaction to run in toluene, has never been reported. As the promoting effect of an added carboxylic acid, especially 1-naphthoic acid, is unknown.

References for Example 2
(1) Pellon, R. F.; Carrasco, R.; Millian, V.; Rodes, L. *Synth. Commum.* 1995, 25, 1077–1083 and references cited therein.
(2) For a review, see Evans, D. A.; DeVries, K. M. In *Glycopeptide Antibiotics, Drugs and the Pharmaceutical Sciences*; Nagarijan, R., Ed.: Marcel Decker, Inc.: New York, 1994 Vol 63, pp-63–104.
(3) *J. Antibiot.* 1987, 40, 450–454
(4) *J. Antibiot.* 1986, 39, 1674–1684; *J. Antibiot.* 1986, 39, 1685–1696; *J. Antibiot.* 1986, 39, 1696–1703.
(5) *J. Am. Chem. Soc.* 1983, 105, 1343; *J. Am. Chem. Soc.* 1977, 99, 8040.
(6) *Chem. Pharm. Bull.* 1984,32, 284; *Chem. Pharm. Bull* 1983, 31, 1424.
(7) William, D. H. Acc. *Chem. Res.* 1984, 17, 364–369.
(8) Janetka, J. W.; Ramana, P.; Satyshur, K.; Flentke, G. R.; rich, D. H. *J. Am. Chem Soc.* 1997, 119, 441–442.
(9) Ullmann, F. *Ber.* 1904, 37, 853.
(10) Lindley, J. *Tetrahedron* 1984, 40, 1433–1456.

EXAMPLE 3
Copper-catalyzed N-Arylation of Amides

The use of catalytic quantities of dibenzylidene acetone (dba) and 1,10-phenanthroline (phen) promote the copper catalyzed N-arylation of various amides with aryl bromides.

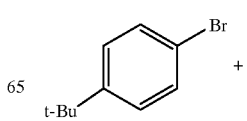

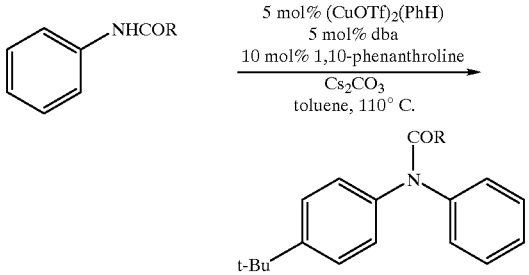

The yields for various permutations of the reaction conditions, as assessed by gas chromatography, are as follows:

| Amide (R) | without dba + phen | with phen | with dba + phen |
|---|---|---|---|
| H | <5 | — | 89 |
| CH$_3$ | <5 | 15 | 97 (83% isolated) |
| C$_6$H$_5$ | 0 | — | 67 |

2,2'-Bipyridine was also found to be an effective ligand for this arylation, although it was not as effective as 1,10-phenanthroline.

EXAMPLE 4

Synthesis of 4Chloro-3',4'-dimethyldiphenylether

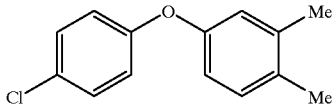

1-Chloro-4-iodobenzene(2.5 mmol), 3,4-dimethylphenol (3.5 or 5.0 mmol), Cs$_2$CO$_3$ (3.5 or 5.0 mmol), (CuOTf)$_2$.PhH (0.0625 mmol, 5.0 mol % Cu), ethyl acetate (0.125 mmol, 5.0 mol %), and toluene (2.0 mL) were added to an oven-dried test tube which was then sealed with a septum, purged with argon, and heated to 110 C under argon until the aryl halide was consumed as determined by GC analysis. The reaction mixture was then allowed to cool to room temperature, diluted with Et$_2$O and washed sequentially with 5% aqueous NaOH, water and brine. The organic layer was dried over Mg$_2$SO$_4$ and concentrated under vacuum to give the crude product. Purification by flash column chromatography (1% Et$_2$O/pentane) gave the analytically pure product as a clear oil (530 mg, 91% yield). $^1$H NMR (300 MHz, CDCl$_3$) δ 7.22 (d, J=8.5 Hz, 2H), 7.07 (d, J=8.3 Hz, 1H), 6.88 (d, J=8.5 Hz, 2H), 6.79 (br s, 1H), 6.73 (br d, J=8.3 Hz, 1H), 2.22 (s, 6H); $^{13}$C NMR (75 MHz, CDCl$_3$) δ 156.7, 154.5, 138.3, 131.9, 130.9, 129.5, 127.5, 120.5, 119.4, 116.5, 19.8, 18.9; IR (neat): 3025, 2931, 2851, 1878, 1584, 1490, 1249, 1155, 1091, 1002 cm$^{-1}$. Anal. Calcd for C$_{14}$H$_{13}$OCl: C, 72.26; H, 5.63. Found: C, 72.42; H, 5.54. Using 0.25 mol % (CuOTf)$_2$ PhH the yield was 89%.

EXAMPLE 5

Synthesis of Ethyl 4-(3',4'-dimethylphenoxy)benzoate

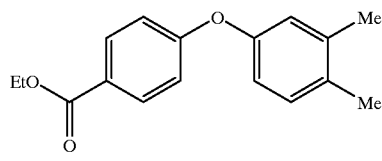

Ethyl 4-bromobenzoate (2.5 mmol), 3,4-dimethylphenol (3.5 or 5.0 mmol), molecular sieves (625 mg), Cs$_2$CO$_3$ (3.5 or 5.0 mmol), (CuOTf)$_2$.PhH (0.0625 mmol, 5.0 mol % Cu), ethyl acetate (0.125 mmol, 5.0 mol %), and toluene (2.0 mL) were added to an oven-dried test tube which was then sealed with a septum, purged with argon, and heated to 110 C under argon until the aryl halide was consumed as determined by GC analysis. The reaction mixture was then allowed to cool to room temperature, diluted with Et$_2$O and washed sequentially with 5% aqueous NaOH, water and brine. The organic layer was dried over Mg$_2$SO$_4$ and concentrated under vacuum to give the crude product. Purification by flash column chromatography (1% Et$_2$O/pentane) gave the analytically pure product as a clear oil (425 mg, 63% yield). $^1$H NMR (300 MHz, CDCl$_3$) δ 7.98 (d, J=8.6 Hz, 2H), 7.12 (d, J 8.0 Hz, 1H), 6.95 (d, J=8.6 Hz, 2H), 6.85 (d, J=2.4 Hz, 1H), 6.79 (dd, J=8.0 Hz, 2.3 Hz, 1H), 4.35 (q, J=7.0 Hz, 2H), 2.25 (s, 6H), 1.37 (t, J=7.0 Hz, 3H); $^{13}$C NMR (75 MHz, CDCl$_3$) δ 166.1, 162.2, 153.3, 138.5, 132.8, 131.5, 130.8, 124.4, 121.3, 117.4, 116.8, 60.7, 19.9, 19.1, 14.3; IR (neat): 2978, 2931, 1713, 1595, 1495, 1367, 1261, 1226, 1161, 1102 cm$^{-1}$. Anal. Calcd for C$_{17}$H$_{18}$O$_3$: C, 75.53; H, 6.71. Found: C, 75.77; H, 6.67.

EXAMPLE 6

Synthesis of 3,4,4'-trimethyidiphenylether

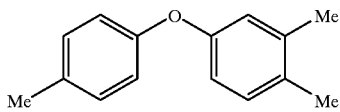

4-Iodotoluene (2.5 mmol), 3,4-dimethylphenol (3.5 or 5.0 mmol), Cs$_2$CO$_3$ (3.5 or 5.0 mmol), (CuOTf)$_2$.PhH (0.0625 mmol, 5.0 mol % Cu), ethyl acetate (0.125 mmol. 5.0 mol %), and toluene (2.0 mL) were added to an oven-dried test tube which was then sealed with a septum, purged with argon, and heated to 110 C under argon until the aryl halide was consumed as determined by GC analysis. The reaction mixture was then allowed to cool to room temperature, diluted with Et$_2$O and washed sequentially with 5% aqueous NaOH, water and brine. The organic layer was dried over Mg$_2$SO$_4$ and concentrated under vacuum to give the crude product. Purification by flash column chromatography (1% Et$_2$O/pentane) gave the analytically pure product as a clear oil (458 mg, 86% yield). $^1$H NMR (300 MHz, CDCl$_3$) δ 7.11 (d, J=8.3 Hz, 2H), 7.06 (d, J=8.1 Hz, 1H), 6.88 (d, J=8.2 Hz, 2H), 6.80 (br s, 1H), 6.73 (br d, J=8.3 Hz, 1H), 2.32 (s, 3H), 2.22 (s, 6H); $^{13}$C NMR (75 MHz, CDCl$_3$) δ 155.4, 155.3 138.0, 132.2, 131.0, 130.5, 130.1, 119.9, 118.5, 115.9, 20.6, 19.8, 18.9; IR (neat): 2919, 2849, 1608, 1496, 1449, 1249, 1214, 1161 cm$^{-1}$. Anal. Calcd for C$_{15}$H$_{16}$O: C, 85.87; H, 7.60. Found: C, 85.69; H, 7.68. Using 0.25 mol % (CuOTf)$_2$ PhH the yield was 72%.

EXAMPLE 7

Syntheses of 3',4'-dimethyl-4-tert-butyldiphenylether

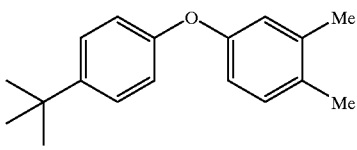

4-tert-Butylbromobenzene or 4-tertbutyliodobenzene (2.5 mmol), 3,4-dimethylphenol (3.5 or 5.0 mmol), $Cs_2CO_3$ (3.5 or 5.0 mmol), $(CuOTf)_2 \cdot PhH$ (0.0625 mmol, 5.0 mol % Cu), ethyl acetate (0.125 mmol, 5.0 mol %), and toluene (2.0 mL) were added to an oven-dried test tube which was then sealed with a septum, purged with argon, and heated to 110 C under argon until the aryl halide was consumed as determined by GC analysis. The reaction mixture was then allowed to cool to room temperature, diluted with $Et_2O$ and washed sequentially with 5% aqueous NaOH, water and brine. The organic layer was dried over $Mg_2SO_4$ and concentrated under vacuum to give the crude product. Purification by flash column chromatography (pentane) gave the analytically pure product as a clear oil (575 mg, 90% yield for the iodo compound; 550 mg, 86% yield for the bromo compound). $^1$H NMR (300 MHz, $CDCl_3$) δ 7.11 (d, J=8.5 Hz, 2H), 7.06 (d, J=8.4 Hz, 1H), 6.90 (d, J=8.4 Hz, 2H), 6.82 (br s, 1H), 6.74 (br d, J=8.3 Hz, 1H), 2.22 (s, 6H), 1.31 (s, 9H); $^{13}$C NMR (75 MHz, $CDCl_3$) δ 155.4, 155.2, 145.4, 138.0, 131.1, 130.5, 126.3, 120.3, 117.9, 116.2, 34.2, 41.4, 19.9 19.1; IR (neat): 2956, 2867, 1600, 1496, 1452, 1253, 1216, 1179, 1105, 1002 $cm^{-1}$. Anal. Calcd for $C_{18}H_{22}O$: C, 84.99; H$^i$ 8.72. Found: C, 85.23; H, 8.85.

EXAMPLE 8

Synthesis of 3',4'-Dimethyl-4-methoxydiphenylether

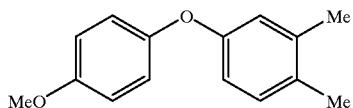

4-Iodoanisole (2.5 mmol), 3,4-dimethylphenol (3.5 or 5.0 mmol), $Cs_2CO_3$ (3.5 or 5.0 mmol), $(CuOTf)_2 \cdot PhH$ (0.0625 mmol, 5.0 mol % Cu), ethyl acetate (0.125 mmol, 5.0 mol %), and toluene (2.0 mL) were added to an oven-dried test tube which was then sealed with a septum, purged with argon, and heated to 110 C under argon until the aryl halide was consumed as determined by GC analysis. The reaction mixture was then allowed to cool to room temperature, diluted with $Et_2O$ and washed sequentially with 5% aqueous NaOH, water and brine. The organic layer was dried over $Mg_2SO_4$ and concentrated under vacuum to give the crude product. Purification by flash column chromatography (1% $Et_2O$/pentane) gave the analytically pure product as a clear oil (445 mg, 78% yield). $^1$H NMR (300 MHz, $CDCl_3$) δ 7.03 (d, J=8.1 Hz, 1H), 6.94 (d, J=8.2 Hz, 2H), 6.85 (d, J=8.2 Hz, 2H), 6.75 (br s, 1H), 6.68 (br d, J=8.3 Hz, 1H), 3.77 (s, 3H), 2.20 (s, 6H); $^{13}$C NMR (75 MHz, $CDCl_3$) δ 156.1, 155.5, 150.6, 137.9, 130.5, 130.4, 120.1, 119.1, 115.0, 114.8, 55.3, 19.8, 18.8; IR (neat): 2931, 2837, 1508, 1496, 1455, 1284, 1226, 1179, 1149, 1102, 1032 $cm^{-1}$. Anal. Calcd for $C_{15}H_{16}O_2$: C, 78.92; H, 7.06. Found: C, 79.12; H, 7.16.

EXAMPLE 9

Synthesis of 3',4'-Dimethyl-4-(N,N-dimethylamino)diphenylether

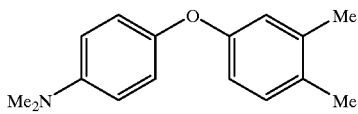

4-Bromo-N,N-dimethylaniline (2.5 mmol), 3,4-dimethylphenol (3.5 or 5.0 mmol), $Cs_2CO_3$ (3.5 or 5.0 mmol), $(CuOTf)_2 \cdot PhH$ (0.0625 mmol, 5.0 mol % Cu), ethyl acetate (0.125 mmol, 5.0 mol %), and toluene (2.0 mL) were added to an oven-dried test tube which was then sealed with a septum, purged with argon, and heated to 110 C under argon until the aryl halide was consumed as determined by GC analysis. The reaction mixture was then allowed to cool to room temperature, diluted with $Et_2O$ and washed sequentially with 5% aqueous NaOH, water and brine. The organic layer was dried over $Mg_2SO_4$ and concentrated under vacuum to give the crude product. Purification by flash column chromatography (5% EtOAc/hexane) gave the analytically pure product as a clear oil (561 mg, 83% yield). $^1$H NMR (300 MHz, $CDCl_3$) δ 7.02 (d, J=8.1 Hz, 1H), 6.91–6.96 (m, 2H), 6.65–6.75 (m, 4H), 2.92 (s, 6H), 2.20 (s, 6H); $^{13}$C NMR (75 MHz, $CDCl_3$) δ 157.0, 148.6, 147.6, 137.7, 130.4, 130.1, 120.4, 119.1, 115.0, 114.2, 41.2, 19.7, 18.7; IR (neat): 2973, 2913, 1677, 1606, 1515, 1496, 1445, 1355, 1249, 1224 $cm^{-1}$. Anal. Calcd for $C_{16}H_{18}O$: C, 84.91; H, 8.02. Found: C, 85.07; H, 7.97.

EXAMPLE 10

Synthesis of 3,3',4.5'-tetramethyldiphenylether

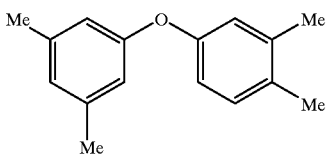

5-Iodo-1,3-dimethylbenzene (2.5 mmol), 3,4-dimethylphenol (3.5 or 5.0 mmol), $Cs_2CO_3$ (3.5 or 5.0 mmol), $(CuOTf)_2 \cdot PhH$ (0.0625 mmol, 5.0 mol % Cu), ethyl acetate (0.125 mmol, 5.0 mol %), and toluene (2.0 mL) were added to an oven-dried test tube which was then sealed with a septum, purged with argon, and heated to 110 C under argon until the aryl halide was consumed as determined by GC analysis. The reaction mixture was then allowed to cool to room temperature, diluted with $Et_2O$ and washed sequentially with 5% aqueous NaOH, water and brine. The organic layer was dried over $Mg_2SO_4$ and concentrated under vacuum to give the crude product. Purification by flash column chromatography (0.7% $Et_2O$/pentane) gave the analytically pure product as a clear oil (513 mg, 91% yield). $^1$H NMR (300 Mhz, $CDCl_3$) δ 7.06 (d, J=8.2 Hz, 1H), 6.81 (br s 1H), 6.74 (d, J=8.2 Hz, 1H), 6.69 (br s, 1H), 6.60 (br s, 2H), 2.26 (s, 6H), 2.22 (s, 6H); $^{13}$C NMR (75 MHz, $CDCl_3$) δ 157.8, 155.0, 139.4, 138.0, 131.3, 130.5, 125.4, 120.5, 116.4, 116.0, 21.3, 19.9, 19.0; IR (neat): 3025, 2919, 2849, 1596, 1496, 1461, 1302, 1244, 1196, 1155, 1026 $cm^{-1}$. Anal. Calcd for $C_{16}H_{18}O$: C, 84.91; H, 8.02. Found: C, 85.07; H, 7.97.

EXAMPLE 11
Synthesis of 2,3',5'-trimethyldiphenylether

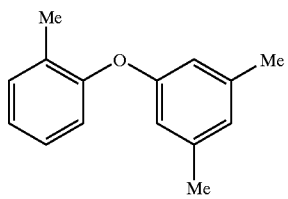

5-Iodo-1,3-dimethylbenzene (2.5 mmol), o-cresol (3.5 or 5.0 mmol), Cs$_2$CO$_3$ (3.5 or 5.0 mmol), (CuOTf)$_2$.PhH (0.0625 mmol, 5.0 mol % Cu), ethyl acetate (0.125 mmol, 5.0 mol %), and toluene (2.0 mL) were added to an oven-dried test tube which was then sealed with a septum, purged with argon, and heated to 110 C under argon until the aryl halide was consumed as determined by GC analysis. The reaction mixture was then allowed to cool to room temperature, diluted with Et$_2$O and washed sequentially with 5% aqueous NaOH, water and brine. The organic layer was dried over Mg$_2$SO$_4$ and concentrated under vacuum to give the crude product. Purification by flash column chromatography (1% Et$_2$O/pentane) gave the analytically pure product as a clear oil (463 mg, 87% yield). $^1$H NMR (300 MHz, CDCl$_3$) δ 7.24 (d, J=6.5 Hz, 1H), 7.16 (t, J=7.5 Hz, 1H), 7.05 (t, J–7.3 Hz, 1H), 6.89 (d, J=8.0 Hz, 1H), 6.69 (s, 1H), 6.53 (s, 2H), 2.26 (s, 6H), 2.24 (s, 3H); $^{13}$C NMR (75 MHz, CDCl$_3$) δ 157.9, 154.6, 139.5, 131.3, 129.9, 127.1, 1224.1, 123.7, 119.7, 115.0, 21.3, 16.2; IR (neat): 2919, 1584, 1490, 1378, 1302, 1226, 1185, 1138, 1108, 1026 cm$^{-1}$. Anal. Calcd for C$_{15}$H$_{16}$O: C, 84.87; H, 7.60. Found: C, 84.99; H, 7.66.

EXAMPLE 12
Synthesis of 3,4',5-Trimethyldiphenylether

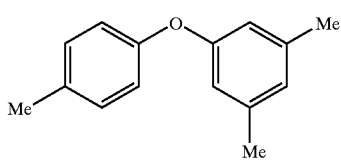

5-Iodo-1,3-dimethylbenzene (2.5 mmol), p-cresol (3.5 or 5.0 mmol), Cs$_2$CO$_3$ (3.5 or 5.0 mmol), (CuOTf)$_2$.PhH (0.0625 mmol, 5.0 mol % Cu), ethyl acetate (0.125 mmol, 5.0 mol %), and toluene (2.0 mL) were added to an oven-dried test tube which was then sealed with a septum, purged with argon, and heated to 110 C under argon until the aryl halide was consumed as determined by GC analysis. The reaction mixture was then allowed to cool to room temperature, diluted with Et$_2$O and washed sequentially with 5% aqueous NaOH, water and brine. The organic layer was dried over Mg$_2$SO$_4$ and concentrated under vacuum to give the crude product. Purification by flash column chromatography (pentane) gave the analytically pure product as a clear oil (155 mg, 29% yield). Using procedure B, the yield was 80%. $^1$H NMR (300 MHz, CDCl$_3$) δ 7.13 (d, J=8.3 Hz, 2H), 6.91 (t, J=8.2 Hz, 2H), 6.71 (s, 1H), 6.61 (s, 2H), 2.33 (s, 3H), 2.27 (s, 6H); $^{13}$C NMR (75 MHz, CDCl$_3$) δ 157.8, 154.9, 139.5, 132.7, 130.2, 124.6, 119.1, 116.1, 21.3, 20.7; IR (neat): 3025, 2919, 2861, 1590, 1502, 1467, 1302, 1220, 1161, 1132, 1102, 1020 cm$^{-1}$. Anal. Calcd for C$_{15}$H$_{16}$O: C, 84.87; H, 7.60. Found: C, 85.00; H, 7.80.

EXAMPLE 13
Synthesis of 2,2',5-Trimethyldiphenylether

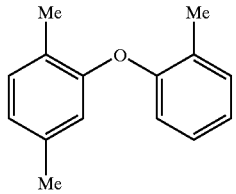

1-Iodo-2,5-dimethylbenzene (2.5 mmol), o-cresol (3.5 or 5.0 mmol), Cs$_2$CO$_3$ (3.5 or 5.0 mmol), (CuOTf)$_2$.PhH (0.0625 mmol, 5.0 mol % Cu), ethyl acetate (0.125 mmol, 5.0 mol %), and toluene (2.0 mL) were added to an oven-dried test tube which was then sealed with a septum, purged with argon, and heated to 110 C under argon until the aryl halide was consumed as determined by GC analysis. The reaction mixture was then allowed to cool to room temperature, diluted with Et$_2$O and washed sequentially with 5% aqueous NaOH, water and brine. The organic layer was dried over Mg$_2$SO$_4$ and concentrated under vacuum to give the crude product. Purification by flash column chromatography (hexane) gave the analytically pure product as a clear oil (448 mg, 84% yield). $^1$H NMR (300 MHz, CDCl$_3$) δ 7.21 (d, J=7.3 Hz, 1H), 7.08 (t, J=7.3 Hz, 2H), 6.97 (t, J=7.3 Hz, 1H), 6.80 (d, J=7.8 Hz, 1H), 6.69 (d, J=8.0 Hz, 1H), 6.55 (s, 1H), 2.28 (s, 3H), 2.22 (s, 6H); $^{13}$C NMR (75 MHz, CDCl$_3$) δ 155.4, 154.9, 136.9, 131.2, 131.0, 128.6, 126.9, 125.7, 123.8, 122.8, 118.5, 117.4, 21.0, 16.1, 15.7; IR (neat): 3024, 2922, 2860, 1578, 1506, 1490, 1255, 1227, 1186, 1121 cm$^{-1}$. Anal. Calcd for C$_{15}$H$_{16}$O: C, 84.87; H, 7.60. Found: C, 85.11; H, 7.75.

EXAMPLE 14
Synthesis of 2-(3',4'-Dimethylphenoxy)benzoic Acid

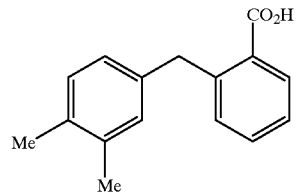

2-Bromobenzoic acid (2.5 mmol), 3,4-dimethylphenol (3.5 or 5.0 mmol), Cs$_2$CO$_3$ (3.5 or 5.0 mmol), (CuOTf)$_2$.PhH (0.0625 mmol, 5.0 mol % Cu), ethyl acetate (0.125 mmol, 5.0 mol %), and toluene (2.0 mL) were added to an oven-dried test tube which was then sealed with a septum, purged with argon, and heated to 110 C under argon until the aryl halide was consumed as determined by GC analysis. The reaction mixture was then allowed to cool to room temperature, diluted with Et$_2$O and washed sequentially with 5% aqueous NaOH, water and brine. The organic layer was dried over Mg$_2$SO$_4$ and concentrated under vacuum to give the crude product. Purification by flash column chromatography (20% Et$_2$O/pentane) gave the analytically pure product as a white solid (466 mg, 77% yield), mp: 98 C. $^1$H NMR (300 MHz, CDCl$_3$) δ 8.18 (d, J=8.0 Hz, 1H), 7.45 (t, J=7.9 Hz, 1H), 7.20–7.15 (m, 2H), 6.90–6.83 (m, 3 H), 2.25 (s, 6H); $^{13}$C NMR (75 MHz, CDCl$_3$) δ 167.2, 157.7, 152.5, 138.8, 134.9, 133.8, 133.1, 130.9, 123.1, 121.2, 119.4, 117.6, 117.3, 19.9, 19.0; IR (KBr): 2931, 2590, 1685, 1596, 1572, 1482, 1402, 1302, 1243, 1214, 1149 cm$^{-1}$. Anal. Calcd for C$_{15}$H$_{14}$O$_2$: C, 84.91; H, 8.02. Found: C, 84.77.99; H, 8.16.

EXAMPLE 15
Synthesis of 2-Isopropyl-4'-methyldiphenylether

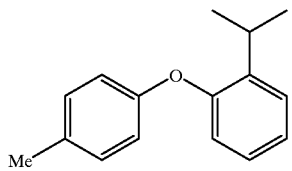

4-Iodotoluene (2.5 mmol), 2-isopropylphenol (3.5 or 5.0 mmol), $Cs_2CO_3$ (3.5 or 5.0 mmol), $(CuOTf)_2 \cdot PhH$ (0.0625 mmol, 5.0 mol % Cu), ethyl acetate (0.125 mmol, 5.0 mol %), and toluene (2.0 mL) were added to an oven-dried test tube which was then sealed with a septum, purged with argon, and heated to 110 C under argon until the aryl halide was consumed as determined by GC analysis. The reaction mixture was then allowed to cool to room temperature, diluted with $Et_2O$ and washed sequentially with 5% aqueous NaOH, water and brine. The organic layer was dried over $Mg_2SO_4$ and concentrated under vacuum to give the crude product. Purification by flash column chromatography (hexane) gave the analytically pure product as a clear oil (428 mg, 76% yield). $^1H$ NMR (300 MHz, $CDCl_3$) δ 7.28–7.32 (m, 1H), 7.03–7.12 (m, 4H), 6.79–6.85 (m, 3H), 3.32 (septet, J=7.0 Hz, 1H), 2.28 (s, 3H), 1.22 (d, J=7.1 Hz, 1H); $^{13}C$ NMR (75 MHz, $CDCl_3$) δ 155.5, 151.3, 145.7, 131.9, 129.9, 124.3, 121.0, 120.4, 117.4, 112.9, 55.9, 20.5; IR (neat): 3026, 2941, 2868, 1506. 1490, 1265, 1188, 1120 $cm^{-1}$. Anal. Calcd for $C_{16}H_{18}O$: C, 84.91; H, 8.02. Found: C, 84.77; H, 8.16.

EXAMPLE 16
Synthesis of 2',5'-Dimethyl-2-isopropyldiphenylether

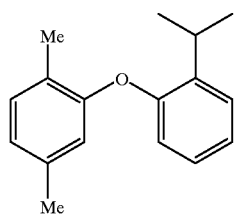

1-Iodo-2,5-dimethylbenzene (2.5 mmol), 2-isopropylphenol (3.5 or 5.0 mmol), $Cs_2CO_3$ (3.5 or 5.0 mmol), $(CuOTf)_2 \cdot PhH$ (0.0625 mmol, 5.0 mol % Cu), ethyl acetate (0.125 mmol, 5.0 mol %), and toluene (2.0 mL) were added to an oven-dried test tube which was then sealed with a septum, purged with argon, and heated to 110 C under argon until the aryl halide was consumed as determined by GC analysis. The reaction mixture was then allowed to cool to room temperature, diluted with $Et_2O$ and washed sequentially with 5% aqueous NaOH, water and brine. The organic layer was dried over $Mg_2SO_4$ and concentrated under vacuum to give the crude product. Purification by flash column chromatography (hexane) gave the analytically pure product as a clear oil (500 mg, 83% yield). $^1H$ NMR (300 MHz, $CDCl_3$) δ 7.32 (dd, J=2.2, 7.1 Hz, 3H), 7.02–7.13 (m, 3H), 6.82 (d, J=7.2 Hz, 1H), 6.67 (dd, J=2.1, 7.2 Hz, 1H), 6.58 (s, 1H), 3.35 (septet, J=6.8 Hz, 1H), 2.23 (s, 6H), 1.27 (d, J=6.6 Hz, 6H); $^{13}C$ NMR (75 MHz, $CDCl_3$) δ 155.2, 154.5, 138.8, 137.0, 131.0, 126.72, 126.66, 125.9, 123.8, 122.9, 118.7, 117.3, 27.2, 22.9, 21.0, 15.8; IR (neat): 3029, 2961, 2868, 1620, 1576, 1506, 1490, 1449, 1282, 1188, 1120 $cm^{-1}$. Anal. Calcd for $C_{17}H_{20}O$: C, 84.96; H, 8.39. Found: C, 84.72; H, 8.24.

EXAMPLE 17
Synthesis of 2-Methoxy-4'-methyldiphenylether

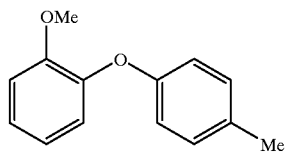

2-Bromoanisole (2.5 mmol), p-cresol (3.5 or 5.0 mmol), $Cs_2CO_3$ (3.5 or 5.0 mmol), $(CuOTf)_2$ PhH (0.0625 mmol, 5.0 mol % Cu), ethyl acetate (0.125 mmol, 5.0 mol %), 1-naphthoic acid (3.5 mmol), molecular sieves (625 mg) and toluene (1.5 mL) were added to an oven-dried test tube which was then sealed with a septum, purged with argon, and heated to 110 C under argon until the aryl halide was consumed as determined by GC analysis. Upon cooling at room temperature, dichloromethane was added and the solvent was removed by filtration. The remaining molecular sieves were stirred with another portion of dichloromethane for 1 h at room temperature, and the solvent was removed by filtration. The combined organic phases were washed with 5% aqueous NaOH. The aqueous layer was then extracted three times with dichloromethane and the combined organic layers were washed with brine. The organic layer was dried over $Mg_2SO_4$ and concentrated under vacuum to give the crude product. Purification by flash column chromatography (2% EtOAc/hexane) gave the analytically pure product as a clear oil (429 mg, 81% yield). $^1H$ NMR (300 MHz, $CDCl_3$)δ 6 7.11–7.15 (m, 3H), 6.88–7.03 (m, 4H), 3.87 (s, 3H), 2.34 (s, 3H); $^{13}C$ NMR (75 MHz, $CDCl_3$) δ 156.0, 154.1, 139.9, 131.8, 130.1, 126.81, 126.76, 123.8, 119.3, 117.7, 27.1, 23.0, 20.6; IR (neat): 3021, 2955, 1610, 1590, 1508, 1219, 1110, 1020 $cm^{-1}$. Anal. Calcd for $C_{14}H_{14}O_2$: C, 78.48; H, 6.59. Found: C, 78.27; H, 6.52.

EXAMPLE 18
Synthesis of 4-Phenoxybenzonitrile

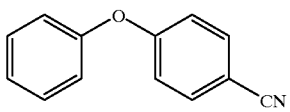

4-Bromobenzonitrile (2.5 mmol), phenol (3.5 or 5.0 mmol), $Cs_2CO_3$ (3.5 or 5.0 mmol), $(CuOTf)_2$ PhH (0.0625 mmol, 5.0 mol % Cu), ethyl acetate (0.125 mmol, 5.0 mol %), 1-naphthoic acid (3.5 mmol), molecular sieves (625 mg) and toluene (1.5 mL) were added to an oven-dried test tube which was then sealed with a septum, purged with argon, and heated to 110 C under argon until the aryl halide was consumed as determined by GC analysis. Upon cooling at room temperature, dichloromethane was added and the solvent was removed by filtration. The remaining molecular sieves were stirred with another portion of dichloromethane for 1 h at room temperature, and the solvent was removed by filtration. The combined organic phases were washed with 5% aqueous NaOH. The aqueous layer was then extracted three times with dichloromethane and the combined organic layers were washed with brine. The organic layer was dried over $Mg_2SO_4$ and concentrated under vacuum to give the crude product. Purification by flash column chromatography (3% EtOAc/hexane) gave the analytically pure product as a clear oil (405 mg, 86% yield). $^1H$ NMR (300 MHz, $CDCl_3$) δ 7.57 (d, J=8.7 Hz, 2H), 7.40 (t, J=7.9Hz, 2H), 7.22 (t, J=7.6Hz, 1H), 7.05 (d, J=7.9Hz, 2H), 6.98 (d, J=8.8 Hz, 2H); $^{13}$C NMR (75 MHz, CDCl$_3$) δ 154.6, 133.9, 130.0, 124.9, 120.2, 118.6, 117.7, 105.6; IR (neat): 3068, 2226, 1586, 1483, 1245, 1165 cm$^{-1}$.

EXAMPLE 19
Synthesis of 4-Phenoxy-tert-butylbenzene

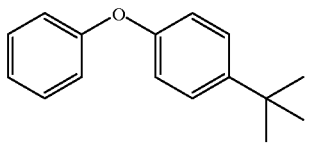

4-t-Butylbromobenzene (2.5 mmol), phenol (3.5 or 5.0 mmol), Cs$_2$CO$_3$ (3.5 or 5.0 mmol), (CuOTf)$_2$ PhH (0.0625 mmol, 5.0 mol % Cu), ethyl acetate (0.125 mmol, 5.0 mol %), 1-naphthoic acid (3.5 mmol), molecular sieves (625 mg) and toluene (1.5 mL) were added to an oven-dried test tube which was then sealed with a septum, purged with argon, and heated to 110 C under argon until the aryl halide was consumed as determined by GC analysis. Upon cooling at room temperature, dichloromethane was added and the solvent was removed by filtration. The remaining molecular sieves were stirred with another portion of dichloromethane for 1 h at room temperature, and the solvent was removed by filtration. The combined organic phases were washed with 5% aqueous NaOH. The aqueous layer was then extracted three times with dichloromethane and the combined organic layers were washed with brine. The organic layer was dried over Mg$_2$SO$_4$ and concentrated under vacuum to give the crude product. Purification by flash column chromatography (2% EtOAc/hexane) gave the analytically pure product as a clear oil (457 mg, 81% yield). $^1$H NMR (300 MHz, CDCl$_3$) δ 7.22–7.34 (m, 4H), 6.90–7.05 (m, 5H), 1.30 (s, 9H); $^{13}$C NMR (75 MHz, CDCl$_3$) δ 157.6, 154.7, 146.0, 129.6, 126.5, 122.9, 118.6, 118.5, 34.3, 31.5; IR (neat): 3068, 3962, 8867, 1590, 1508, 1489, 1240 cm$^{-1}$.

EXAMPLE 20
Synthesis of 4-(4'-Chlorophenoxy)acetophenone

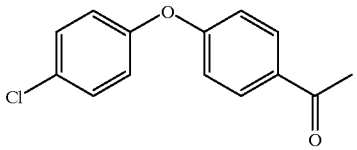

4-Iodoacetophenone (2.5 mmol), p-chlorophenol (3.5 or 5.0 mmol), Cs$_2$CO$_3$ (3.5 or 5.0 mmol), (CuOTf)$_2$ PhH (0.0625 mmol, 5.0 mol % Cu), ethyl acetate (0.125 mmol, 5.0 mol %), 1-naphthoic acid (3.5 mmol), molecular sieves (625 mg) and toluene (1.5 mL) were added to an oven-dried test tube which was then sealed with a septum, purged with argon, and heated to 110 C under argon until the aryl halide was consumed as determined by GC analysis. Upon cooling at room temperature, dichloromethane was added and the solvent was removed by filtration. The remaining molecular sieves were stirred with another portion of dichloromethane for 1 h at room temperature, and the solvent was removed by filtration. The combined organic phases were washed with 5% aqueous NaOH. The aqueous layer was then extracted three times with dichloromethane and the combined organic layers were washed with brine. The organic layer was dried over Mg$_2$SO$_4$ and concentrated under vacuum to give the crude product. Purification by flash column chromatography (4% EtOAc/hexane) gave the analytically pure product as a light yellow solid (580 mg, 94%) yield), mp: 51–53 C. $^1$H NMR (300 MHz, CDCl$_3$) δ 7.91–7.96 (m, 2H), 7.31–7.36 (m, 2H), 6.96–7.02 (m, 4H), 2.56 (s, 3H); $^{13}$C NMR (75 MHz, CDCl$_3$) δ 196.5, 161.5, 154.3, 132.4, 130.7, 130.7, 129.8, 121.4, 117.5, 26.5; IR(KBr): 2955, 1676, 1600, 1504, 1358, 1254, 1086 cm$^{-1}$. Anal. Calcd for C$_{14}$H$_{11}$O$_2$Cl : C, 68.16; H, 4.49. Found: C, 67.95; H, 4.64.

EXAMPLE 21
Synthesis of 4-Methyl-4'-chlorodiphenylether

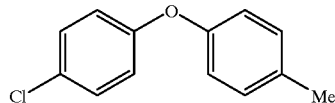

4-Iodotoluene (2.5 mmol), p-chlorophenol (3.5 or 5.0 mmol), Cs$_2$CO$_3$ (3.5 or 5.0 mmol), (CuOTf)$_2$ PhH (0.0625 mmol, 5.0 mol % Cu), ethyl acetate (0.125 mmol, 5.0 mol %), 1-naphthoic acid (3.5 mmol), molecular sieves (625 mg) and toluene (1.5 mL) were added to an oven-dried test tube which was then sealed with a septum, purged with argon, and heated to 110 C under argon until the aryl halide was consumed as determined by GC analysis. Upon cooling at room temperature, dichloromethane was added and the solvent was removed by filtration. The remaining molecular sieves were stirred with another portion of dichloromethane for 1 h at room temperature, and the solvent was removed by filtration. The combined organic phases were washed with 5% aqueous NaOH. The aqueous layer was then extracted three times with dichloromethane and the combined organic layers were washed with brine. The organic layer was dried over Mg$_2$SO$_4$ and concentrated under vacuum to give the crude product. Purification by flash column chromatography (2% EtOAc/hexane) gave the analytically pure product as a white solid (433 mg, 79% yield), mp: 47.5–49 C. $^1$H NMR (300 MHz, CDCl$_3$) δ 7.23 (d, J=8.6 Hz, 2H), 7.12 (d, J=8.4 Hz, 2H), 6.87–6.92 (m, 4H), 2.32 (s, 3H); $^{13}$C NMR (75 MHz, CDCl$_3$) δ 156.4, 154.2, 133.2, 130.2, 129.5, 127.6, 119.4, 119.0, 20.8; IR (KBr): 3096, 3037, 2978, 2872, 1890, 1590, 1480, 1237, 1096 cm$^{-1}$. Anal. Calcd for C$_{13}$H$_{11}$OCl: C, 71.40; H, 5.07. Found: C, 71.67; H, 5.41.

All of the references and publications cited herein are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:
1. The method depicted in scheme 1:

Scheme 1

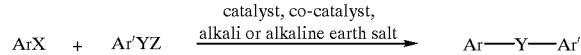

wherein
Ar and Ar' independently represent optionally substituted monocyclic or polycyclic aromatic or heteroaromatic moieties;

X represents Br, I, —O$_3$S(alkyl), or —O$_3$S(aryl);

Y represents O, S, Se, NR, PR, or AsR;

Z represents H, a group that is lost under the reaction conditions to generate a negative charge on Y, or a group that is replaced by H under the reaction conditions;

R represents H, alkyl, aryl, aralkyl, heteroalkyl, heteroaryl, trialkylsilyl, acyl, or sulfonyl;

catalyst is selected from the group consisting of copper carboxylates, copper carbonates, copper sulfates, copper sulfonates, copper halides, copper trifluoroborates, and copper phosphates;

co-catalyst represents an uncharged molecule comprising a Lewis basic pair of electrons;

alkali or alkaline earth salt represents a salt selected from the group consisting of cesium bicarbonate, cesium carbonate, cesium carboxylates, ccsium phosphates, cesiurn alkoxides, cesium silicates, cesium amides, and cesium sulfides;

the reaction takes place at a temperature less than about 150° C.; and the method is not conducted in an amine solvent or an aqueous solvent.

2. The method of claim 1, wherein X represents Br or I.

3. The method of claim 1, wherein Y represents O, S, Se, or NR.

4. The method of claim 1, wherein Y represents O or S.

5. The method of claim 1, wherein Y represents O.

6. The method of claim 1, wherein Z represents H.

7. The method of claim 1, wherein Ar and Ar' independently represent optionally substituted monocyclic aryl or heteroaryl moieties.

8. The method of claim 1, wherein Ar and Ar' independently represent optionally substituted phenyl.

9. The method of claim 1, wherein the reaction occurs in a non-polar, aprotic solvent.

10. The method of claim 1, wherein the reaction occurs in an aromatic hydrocarbon solvent.

11. The method of claim 1, wherein the reaction occurs in toluene.

12. The method of claim 1, wherein the reaction occurs at a temperature in the range of about 75–150 C.

13. The method of claim 1, wherein the reaction occurs at a temperature in the range of about 90–135 C.

14. The method of claim 1, wherein the reaction occurs at a temperature in the range of about 100–120 C.

15. The method of claim 1, wherein the alkali or alkaline earth salt is cesium carbonate.

16. The method of claim 1, wherein the co-catalyst is an ester.

17. The method of claim 1, wherein the co-catalyst is an acetate.

18. The method of claim 1, wherein the co-catalyst is ethyl acetate.

19. The method of claim 1, wherein the catalyst is copper triflate.

20. The method of claim 1, wherein the catalyst and co-catalyst are independently present in the range of about 0.01 to 20 mol % relative to Ar'YZ.

21. The method of claim 1, wherein the catalyst and co-catalyst are independently present in the range of about 0.1 to 10 mol % relative to Ar'YZ.

22. The method of claim 1, wherein the catalyst and co-catalyst are independently present in the range of about 1 to 5 mol % relative to Ar'YZ.

23. The method of claim 1, wherein X represents Br or I; Y represents O, S, Se, or NR; Ar and Ar' independently represent optionally substituted monocyclic aryl or heteroaryl moieties; the reaction occurs in a non-polar, aprotic solvent; the reaction occurs at a temperature in the range of about 75–150 C; the co-catalyst is an ester; and the catalyst and co-catalyst are independently present in the range of about 0.01 to 20 mol % relative to Ar'YZ.

24. The method of claim 1, wherein X represents Br or I; Y represents O or S; the reaction occurs in an aromatic hydrocarbon solvent; the alkali or alkaline earth salt is cesium carbonate; the reaction occurs at a temperature in the range of about 90–135 C; the co-catalyst is an acetate; and the catalyst and co-catalyst are independently present in the range of about 0.1 to 10 mol % relative to Ar'YZ.

25. The method of claim 1, wherein X represents Br or I; Y represents O; Z represents H; the reaction occurs in toluene; the alkali or alkaline earth salt is cesium carbonate, the catalyst is copper triflate; the co-catalyst is ethyl acetate; the reaction occurs at a temperature in the range of about 100–120 C; and the catalyst and co-catalyst are independently present in the range of about 1 to 5 mol % relative to Ar'YZ.

26. The method of claim 2, wherein Y represents O or S.

27. The method of claim 2, wherein Y represents O or S; and the alkali or alkaline earth salt is cesium carbonate.

28. The method of claim 2, wherein Z represents H.

29. The method of claim 2, wherein the co-catalyst is ethyl acetate; the catalyst is copper triflate; the reaction occurs in toluene; and the alkali or alkaline earth salt is cesium carbonate.

30. The method of any one of claim 15–18 and 19–29, wherein the reaction is intramolecular.

31. The method depicted in scheme 2:

Scheme 2

$$ArX + Ar'YZ \xrightarrow{\text{catalyst, co-catalyst,}\\ \text{alkali or alkaline earth salt,}\\ \text{acid activator}} Ar\text{—}Y\text{—}Ar'$$

wherein

Ar and Ar' independently represent optionally substituted monocyclic or polycyclic aromatic or heteroaromatic moieties;

X represents Br, I, —O$_3$S(alkyl), or —O$_3$S(aryl);

Y represents O, S, Se, NR, PR, or AsR;

Z represents H, a group that is lost under the reaction conditions to generate a negative charge on Y, or a group that is replaced by H under the reaction conditions;

R represents H, alkyl, aryl, arallyl, heteroalkyl, heteroaryl, trialkylsilyl, acyl, or sulfonyl;

catalyst is selected from the group consisting of copper carboxylates, copper carbonates, copper sulfates, copper sulfonates, copper halides, copper trifluoroborates, and copper phosphates;

co-catalyst represents a uncharged molecule comprising a Lewis basic pair of electrons;

acid activator is selected from the group consisting of carboxylic acids, amides, hydroxamic acids, phosphoric acids, phosphonic acids, phosphinic acids, sulfonic acids, sulfinic acids, sulfenic acids, alkylboronic acids, arylboronic acids, silicic acids, and thiols; and alkali or alkaline earth salt represents a salt selected from the group consisting of cesium bicarbonate, cesium carbonate, cesium carboxylates, cesium phosphates, cesium alkoxides, cesium silicates, cesium amides, and cesium sulfides; and the reaction takes place at a temperature less than about 150° C.

32. The method of claim 31, wherein X represents Br or I.

33. The method of claim 31, wherein Y represents O, S, Se, or NR.

34. The method of claim 31, wherein Y represents O or S.

35. The method of claim 31, wherein Y represents O.

36. The method of claim 31, wherein Z represents H.

37. The method of claim 31, wherein Ar and Ar' independently represent optionally substituted monocyclic aryl or heteroaryl moieties.

38. The method of claim 31, wherein Ar and Ar' independently represent optionally substituted phenyl.

39. The method of claim 31, wherein the reaction occurs in a non-polar, aprotic solvent.

40. The method of claim 31, wherein the reaction occurs in an aromatic hydrocarbon solvent.

41. The method of claim 31, wherein the reaction occurs in toluene.

42. The method of claim 31, wherein the reaction occurs at a temperature in the range of about 75–150 C.

43. The method of claim 31, wherein the reaction occurs at a temperature in the range of about 90–135 C.

44. The method of claim 31, wherein the reaction occurs at a temperature in the range of about 100–120 C.

45. The method of claim 31, wherein the alkali or alkaline earth salt is cesium carbonate.

46. The method of claim 31, wherein the co-catalyst is an ester.

47. The method of claim 31, wherein the co-catalyst is an acetate.

48. The method of claim 31, wherein the co-catalyst is ethyl acetate.

49. The method of claim 31, wherein the acid activator is selected from the group consisting of alkyl and aryl carboxylic acids, alkyl and aryl phosphonic acids, alkyl and aryl sulfonic acids, and alkyl and aryl boronic acids.

50. The method of claim 31, wherein the acid activator is selected from the group consisting of alkyl and aryl carboxylic acids.

51. The method of claim 31, wherein the acid activator is selected from the group consisting of aryl carboxylic acids.

52. The method of claim 31, wherein the acid activator is 1-naphthoic acid.

53. The method of claim 31, wherein the catalyst is copper triflate.

54. The method of claim 31, wherein the catalyst and co-catalyst are independently present in the range of about 0.01 to 20 mol % relative to Ar'YZ.

55. The method of claim 31, wherein the catalyst and co-catalyst are independently present in the range of about 0.1 to 10 mol % relative to Ar'YZ.

56. The method of claim 31, wherein the catalyst and co-catalyst are independently present in the range of about 1 to 5 mol % relative to Ar'YZ.

57. The method of claim 31, wherein X represents Br or I; Y represents O, S, Se, or NR; Ar and Ar' independently represent optionally substituted monocyclic aryl or heteroaryl moieties; the reaction occurs in a non-polar, aprotic solvent; the reaction occurs at a temperature in the range of about 75–150 C; the acid activator is selected from the group consisting of alkyl and aryl carboxylic acids, alkyl and aryl phosphonic acids, alkyl and aryl sulfonic acids, and alkyl and aryl boronic acids; the co-catalyst is an ester; and the catalyst and co-catalyst are independently present in the range of about 0.01 to 20 mol % relative to Ar'YZ.

58. The method of claim 31, wherein X represents Br or I; Y represents O or S; the reaction occurs in an aromatic hydrocarbon solvent; the alkali or alkaline earth salt is cesium carbonate; the reaction occurs at a temperature in the range of about 90–135 C; the acid activator is selected from the group consisting of alkyl and aryl carboxylic acids; the co-catalyst is an acetate; and the catalyst and co-atalyst are independently present in the range of about 0.1 to 10 mol % relative to Ar'YZ.

59. The method of claim 31, wherein X represents Br or I; Y represents O; Z represents H; the reaction occurs in toluene; the alkali or alkaline earth salt is cesium carbonate; the catalyst is copper triflate; the acid activator is 1-naphthoic acid; the co-catalyst is ethyl acetate; the reaction occurs at a temperature in the range of about 100–120 C; and the catalyst and co-catalyst are independently present in the range of about 1 to 5 mol % relative to Ar'YZ.

60. The method of claim 32, wherein Y represents O or S.

61. The method of claim 32, wherein Y represents O or S; and the alkali or alkaline earth salt is cesium carbonate.

62. The method of claim 32, wherein Z represents H.

63. The method of claim 32, wherein the co-catalyst is ethyl acetate; the catalyst is copper triflate; the reaction occurs in toluene; the acid activator is 1-naphthoic acid; and the alkali or alkaline earth salt is cesium carbonate.

64. The method of any one of claims 31–44, 45–52, 53–63, wherein the reaction is intramolecular.

* * * * *

UNITED STATES PATENT AND TRADEMARK OFFICE
CERTIFICATE OF CORRECTION

PATENT NO. : 6,395,939 B1  
APPLICATION NO. : 09/166760  
DATED : May 28, 2002  
INVENTOR(S) : Marcoux et al.

Page 1 of 1

It is certified that error appears in the above-identified patent and that said Letters Patent is hereby corrected as shown below:

Please delete the paragraph titled "GOVERNMENT SUPPORT" encompassing Column 1, lines 8-13:

"This invention was supported in part with funding provided by the National Science Foundation; the government has certain rights in the invention."

and replace with:

"This invention was made with Government support under Grant No. CHE9421982 awarded by the National Science Foundation. The Government has certain rights in the invention."

Signed and Sealed this  
Tenth Day of May, 2016

Michelle K. Lee  
*Director of the United States Patent and Trademark Office*